United States Patent
Minagawa

(10) Patent No.: US 10,344,109 B2
(45) Date of Patent: *Jul. 9, 2019

(54) SURFACE MODIFICATION METHOD AND SURFACE-MODIFIED ELASTIC BODY

(71) Applicant: SUMITOMO RUBBER INDUSTRIES LTD., Kobe-shi, Hyogo (JP)

(72) Inventor: Yasuhisa Minagawa, Kobe (JP)

(73) Assignee: SUMITOMO RUBBER INDUSTRIES, LTD., Kobe-Shi, Hyogo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/421,319

(22) PCT Filed: Sep. 9, 2013

(86) PCT No.: PCT/JP2013/074219
§ 371 (c)(1),
(2) Date: Feb. 12, 2015

(87) PCT Pub. No.: WO2014/038688
PCT Pub. Date: Mar. 13, 2014

(65) Prior Publication Data
US 2015/0203612 A1 Jul. 23, 2015

(30) Foreign Application Priority Data
Sep. 10, 2012 (JP) .................................. 2012-198886

(51) Int. Cl.
*C08J 7/18* (2006.01)
*B60C 13/00* (2006.01)
(Continued)

(52) U.S. Cl.
CPC ......... *C08F 36/18* (2013.01); *A61M 5/31513* (2013.01); *B60C 1/0016* (2013.01);
(Continued)

(58) Field of Classification Search
CPC ........ C08F 36/18; C08F 2/50; B60C 11/1346; B60C 13/04; B60C 1/0025; B60C 1/0016;
(Continued)

(56) References Cited

U.S. PATENT DOCUMENTS

| 3,418,066 | A | 12/1968 | Caldwell et al. |
| 5,100,689 | A | 3/1992 | Goldberg et al. |

(Continued)

FOREIGN PATENT DOCUMENTS

| CN | 101372538 A | 2/2009 |
| CN | 101565489 A | 10/2009 |

(Continued)

OTHER PUBLICATIONS

JP 10-298320 machine English translation (Ottersbach et al.), pub. Nov. 1998.*

(Continued)

*Primary Examiner* — Jessica M Roswell
(74) *Attorney, Agent, or Firm* — Birch, Stewart, Kolash & Birch LLP

(57) ABSTRACT

The present invention aims to provide methods for surface-modifying a rubber vulcanizate or a thermoplastic elastomer, which can cost-effectively impart a variety of functions, such as sliding properties or biocompatibility, according to the application. The present invention relates to a method for surface-modifying an object of a rubber vulcanizate or a thermoplastic elastomer, the method including: step 1 of forming polymerization initiation points A on the surface of the object; and step 2 of radically polymerizing a non-functional monomer, starting from the polymerization ini- (Continued)

tiation points A, to grow non-functional polymer chains, and further radically polymerizing a fluorine-containing functional monomer to grow fluorine-containing functional polymer chains.

22 Claims, 4 Drawing Sheets

(51) Int. Cl.
| | |
|---|---|
| A61M 5/31 | (2006.01) |
| C08F 2/50 | (2006.01) |
| B60C 11/04 | (2006.01) |
| C08F 36/18 | (2006.01) |
| B60C 1/00 | (2006.01) |
| A61M 5/315 | (2006.01) |
| B60C 13/04 | (2006.01) |
| B60C 11/13 | (2006.01) |

(52) U.S. Cl.
CPC ........ *B60C 1/0025* (2013.01); *B60C 11/1346* (2013.01); *B60C 13/04* (2013.01); *C08F 2/50* (2013.01); *C08J 7/18* (2013.01); *A61M 2207/00* (2013.01); *C08J 2319/00* (2013.01); *C08J 2323/22* (2013.01)

(58) Field of Classification Search
CPC ................ A61M 5/31; A61M 5/31513; A61M 2207/00; C08J 7/18; C08J 2323/22; C08J 2319/00
See application file for complete search history.

(56) References Cited

U.S. PATENT DOCUMENTS

| | | | |
|---|---|---|---|
| 5,154,727 A | 10/1992 | Dyer | |
| 5,340,879 A | 8/1994 | Audenaert et al. | |
| 5,453,467 A | 9/1995 | Bamford et al. | |
| 5,637,460 A | 6/1997 | Swan | |
| 5,688,252 A | 11/1997 | Matsuda et al. | |
| 5,855,623 A | 1/1999 | English et al. | |
| 5,858,545 A | 1/1999 | Everaerts et al. | |
| 5,885,566 A | 3/1999 | Goldberg | |
| 5,889,073 A | 3/1999 | Zhang et al. | |
| 5,967,714 A | 10/1999 | Ottersbach et al. | |
| 6,001,894 A | 12/1999 | Ottersbach et al. | |
| 6,188,075 B1 | 2/2001 | Takayama et al. | |
| 6,203,856 B1 | 3/2001 | Ottersbach et al. | |
| 6,228,172 B1 | 5/2001 | Taylor et al. | |
| 6,358,557 B1 | 3/2002 | Wang et al. | |
| 6,808,738 B2 | 10/2004 | Ditizio et al. | |
| 6,986,868 B2 | 1/2006 | Madsen | |
| 7,348,055 B2 | 3/2008 | Chappa et al. | |
| 8,299,139 B1 | 10/2012 | Taranekar et al. | |
| 8,323,750 B2 | 12/2012 | Yang et al. | |
| 8,840,927 B2 | 9/2014 | Ditizio et al. | |
| 9,339,845 B2 | 5/2016 | Minagawa | |
| 9,469,736 B2* | 10/2016 | Minagawa ............. A63C 5/056 |
| 9,758,605 B2 | 9/2017 | Minagawa | |
| 9,982,105 B2* | 5/2018 | Minagawa ................. C08J 7/18 |
| 2002/0161065 A1 | 10/2002 | DiTizio et al. | |
| 2004/0086568 A1 | 5/2004 | Ditizio et al. | |
| 2004/0106732 A1 | 6/2004 | Tsuji et al. | |
| 2005/0137355 A1 | 6/2005 | Buckanin et al. | |
| 2005/0168685 A1 | 8/2005 | Katagiri et al. | |
| 2006/0155057 A1 | 7/2006 | Hermeling et al. | |
| 2007/0003592 A1 | 1/2007 | Hissink | |
| 2007/0116971 A1 | 5/2007 | Yoshikawa et al. | |
| 2008/0016644 A1 | 1/2008 | Mizote et al. | |
| 2008/0103287 A1 | 5/2008 | Chino et al. | |
| 2008/0312377 A1 | 12/2008 | Schmidt et al. | |
| 2009/0169715 A1 | 7/2009 | Dias et al. | |
| 2009/0239089 A1 | 9/2009 | Agata et al. | |
| 2009/0257022 A1 | 10/2009 | Abe et al. |
| 2010/0053547 A1 | 3/2010 | Baude et al. |
| 2010/0255336 A1 | 10/2010 | Zabinski |
| 2011/0124766 A1 | 5/2011 | Yang et al. |
| 2011/0160357 A1 | 6/2011 | Gerster et al. |
| 2011/0274940 A1 | 11/2011 | Kyomoto et al. |
| 2012/0021151 A1 | 1/2012 | Tatarka et al. |
| 2012/0100369 A1 | 4/2012 | Hanazawa et al. |
| 2013/0158488 A1 | 6/2013 | Weaver et al. |
| 2013/0158518 A1 | 6/2013 | Li et al. |
| 2013/0203883 A1 | 8/2013 | Minagawa |
| 2013/0274367 A1 | 10/2013 | Minagawa et al. |
| 2013/0310772 A1 | 11/2013 | Minagawa |
| 2014/0039084 A1 | 2/2014 | Minagawa |
| 2014/0128493 A1 | 5/2014 | Minagawa |
| 2014/0322468 A1 | 10/2014 | Minagawa |
| 2015/0203612 A1 | 7/2015 | Minagawa |
| 2016/0122488 A1 | 5/2016 | Minagawa |

FOREIGN PATENT DOCUMENTS

| | | |
|---|---|---|
| CN | 102382291 A | 3/2012 |
| CN | 202427397 U | 9/2012 |
| CN | 103242553 A | 8/2013 |
| CN | 104119552 A | 10/2014 |
| EP | 0 872 512 A2 | 10/1998 |
| EP | 2 623 335 A2 | 8/2013 |
| EP | 2 664 627 A1 | 11/2013 |
| EP | 2 796 155 A1 | 10/2014 |
| EP | 2 894 191 A1 | 7/2015 |
| GB | 1120803 A | 7/1968 |
| GB | 1120804 A | 7/1968 |
| JP | 60-221410 A | 11/1985 |
| JP | 61-209667 A | 9/1986 |
| JP | 62-87163 A | 4/1987 |
| JP | 63-92658 A | 4/1988 |
| JP | 5-43634 A | 2/1993 |
| JP | 5-76590 A | 3/1993 |
| JP | 05-179055 A | 7/1993 |
| JP | 6-25450 A | 2/1994 |
| JP | 6-510322 A | 11/1994 |
| JP | 7-100744 B2 | 11/1995 |
| JP | 08-001793 A | 1/1996 |
| JP | 9-31361 A | 2/1997 |
| JP | 9-67457 A | 3/1997 |
| JP | 9-108359 A | 4/1997 |
| JP | 9-313594 A | 12/1997 |
| JP | 10-90500 A | 4/1998 |
| JP | 10-251350 A | 9/1998 |
| JP | 10-298320 A | 11/1998 |
| JP | 11-192305 A | 7/1999 |
| JP | 2000-273229 A | 10/2000 |
| JP | 2001-31871 A | 2/2001 |
| JP | 2001-46956 A | 2/2001 |
| JP | 2001-95621 A | 4/2001 |
| JP | 2002-145971 A | 5/2002 |
| JP | 2002-544346 A | 12/2002 |
| JP | 2003-2903 A | 1/2003 |
| JP | 2003-510378 A | 3/2003 |
| JP | 2004-528418 A | 9/2004 |
| JP | 2004-298220 A | 10/2004 |
| JP | 2005-3817 A | 1/2005 |
| JP | 2005-516736 A | 6/2005 |
| JP | 2005-208290 A | 8/2005 |
| JP | 2005-213516 A | 8/2005 |
| JP | 2005-523981 A | 8/2005 |
| JP | 2005-253538 A | 9/2005 |
| JP | 2007-77286 A | 3/2007 |
| JP | 2007-119563 A | 5/2007 |
| JP | 2007-145884 A | 6/2007 |
| JP | 2007-514861 A | 6/2007 |
| JP | 2007-202965 A | 8/2007 |
| JP | 2008-73883 A | 4/2008 |
| JP | 2009-030074 A | 2/2009 |
| JP | 2009-518479 A | 5/2009 |
| JP | 2009-138169 A | 6/2009 |
| JP | 2009-226718 A | 10/2009 |
| JP | 2009-227842 A | 10/2009 |
| JP | 2010-23710 A | 2/2010 |

(56) References Cited

FOREIGN PATENT DOCUMENTS

| | | |
|---|---|---|
| JP | 2010-508541 A | 3/2010 |
| JP | 2010-142537 A | 7/2010 |
| JP | 2010-142573 A | 7/2010 |
| JP | 2010-150349 A | 7/2010 |
| JP | 4523532 B2 | 8/2010 |
| JP | 2010-216964 A | 9/2010 |
| JP | 2010-229180 A | 10/2010 |
| JP | 2011-42755 A | 3/2011 |
| JP | 2011-67362 A | 4/2011 |
| JP | 2011-188908 A | 9/2011 |
| JP | 2011-189562 A | 9/2011 |
| JP | 2011-208133 A | 10/2011 |
| JP | 2011-219520 A | 11/2011 |
| JP | 2011-241190 A | 12/2011 |
| JP | 2012-105579 A | 6/2012 |
| JP | 2012-162646 A | 8/2012 |
| JP | 2013-159629 A | 8/2013 |
| JP | 2013-159667 A | 8/2013 |
| JP | 2013-208777 A | 10/2013 |
| JP | 2013-237801 A | 11/2013 |
| JP | 2013-237802 A | 11/2013 |
| JP | 2014-31429 A | 2/2014 |
| JP | 2014-31430 A | 2/2014 |
| JP | 2014-108153 A | 6/2014 |
| WO | WO 93/05081 A1 | 3/1993 |
| WO | WO 03/068289 A1 | 8/2003 |
| WO | WO 03/093357 A1 | 11/2003 |
| WO | WO 2007/065721 A2 | 6/2007 |
| WO | WO 2007/072613 A1 | 6/2007 |
| WO | WO 2008/053712 A1 | 5/2008 |
| WO | WO 2010/058848 A1 | 5/2010 |
| WO | WO 2010/131652 A1 | 11/2010 |
| WO | WO 2011/038483 A1 | 4/2011 |
| WO | WO 2012/091169 A1 | 7/2012 |
| WO | WO 2012/165525 A1 | 12/2012 |
| WO | WO 2014/203668 A1 | 12/2014 |

OTHER PUBLICATIONS

Allmér et al., "Surface Modification of Polymers. I. Vapour Phase Photografting with Acrylic Acid," Journal of Polymer Science: Part A: Polymer Chemistry, vol. 26, 1988, pp. 2099-2111.
International Search Report, dated Jul. 24, 2012, for International Application No. PCT/JP2012/064030.
U.S. Non-Final Office Action, dated May 8, 2015, for U.S. Appl. No. 13/756,837.
U.S. Non-Final Office Action, dated Oct. 20, 2014, for U.S. Appl. No. 13/756,837.
U.S. Notice of Allowance, dated Dec. 26, 2014, for U.S. Appl. No. 13/956,974.
U.S. Office Action (Requirement for Restriction/Election), dated May 9, 2014, for U.S. Appl. No. 13/956,974.
U.S. Office Action dated Jun. 24, 2015, for U.S. Appl. No. 14/118,136.
U.S. Office Action dated Sep. 21, 2015, for U.S. Appl. No. 14/107,746.
U.S. Office Action, dated Apr. 17, 2015, for U.S. Appl. No. 13/775,451.
U.S. Office Action, dated Aug. 25, 2014, for U.S. Appl. No. 13/956,974.
International Search Report and Written Opinion of the International Searching Authority, issued in PCT/JP2014/079947, dated Jan. 20, 2015.
International Search Report, dated Feb. 25, 2014, for International Application No. PCT/JP2013/082409.
International Search Report, issued in PCT/JP2014/063268, dated Aug. 19, 2014.
U.S. Office Action, dated Nov. 3, 2016, for U.S. Appl. No. 14/896,096.
International Search Report issued in PCT/JP2013/074219 dated Dec. 3, 2013.
International Search Report and English translation thereof, dated Jan. 21, 2014, for International Application No. PCT/JP2013/081090.
Jinan Haohua Industry Co., Ltd., "Ethanaminum, N,N,N-trimethyl-2-[(2-methyl-1-oxo-2-propen-1-yl)oxy]-, chloride (1:1)," CAS: 5039-78-1, Product Information Inquiry Description, found online on Dec. 27, 2016, pp. 1-2 (3 pages), http://guide7932.guidechem.com/pro-show2436647.html.
"Fundamental of Polymer Chemistry and Physics," edited by Wuji Wei and etc., Chemical Industry Press, Oct. 2011, pp. 59-60 (4 pages total).
English translation of the Chinese Office Action, dated Sep. 22, 2017, for Chinese Application No. 201380044153.X.
International Search Report (Form PCT/ISA/210) for International Application No. PCT/JP2014/082367, dated Mar. 3, 2015, with an English translation.
Written Opinion of the International Searching Authority (Form PCT/ISA/237) for International Application No. PCT/JP2014/082367, dated Mar. 3, 2015, with an English translation.
English translation of Chinese Office Action for Appl. No. 201480032195.6 dated Jan. 24, 2018.
Zhang, J., et al, "Corona Radiation Technology" China Textile Press, May 2003, p. 14.
Odian, "Principles of polymerization," John Wiley & Sons, 4th Ed., 2004, p. 261 (3 pages total).
Placzek et al., "Photosensitizing Properties of Compounds Related to Benzophenone", Acta Derm Venereol, 93, 2013, pp. 30-32.
U.S. Office Action dated Jan. 10, 2019 for U.S. Appl. No. 15/036,100.
International Search Report and English translation for Application No. PCT/JP2015/070547 (PCT/ISA/210) dated Oct. 6, 2015.
Written Opinion of the International Searching Authority and English translation for Application No. PCT/JP2015/070547 (PCT/ISA/237) dated Oct. 6, 2015.

* cited by examiner

SURFACE MODIFICATION METHOD AND SURFACE-MODIFIED ELASTIC BODY

TECHNICAL FIELD

The present invention relates to surface modification methods and surface-modified elastic bodies, such as a gasket for syringes at least partially having a surface modified by such a method and a tire at least partially having a groove surface modified by such a method.

BACKGROUND ART

In view of the importance of sealing properties, elastic bodies (e.g. rubber) are used in parts which slide while maintaining their sealing performance, for example, a gasket which is integrated with a syringe plunger and forms a seal between the plunger and barrel. Such elastic bodies unfortunately have a slight problem with the sliding properties (see Patent Literature 1). Thus, a sliding property improving agent (e.g. silicone oil) is applied to the sliding surface. However, a concern has been raised over the potential adverse effects of silicone oil on recently marketed biopreparations. Meanwhile, gaskets not coated with a sliding property improving agent have poor sliding properties, and thus do not allow plungers to be smoothly pushed, causing them to pulsate during administration. Hence, problems occur, such as an inaccurate injection amount and infliction of pain on patients.

To satisfy these conflicting requirements, sealing properties and sliding properties, a coating technique with a self-lubricating PTFE film has been proposed (see Patent Literature 2). PTFE films, however, are generally expensive and increase the production cost of processed products. Thus, the range of applications of the films is limited. Also, products coated with PTFE films might not be reliable when they are used in applications in which sliding or the like motion is repeated and thus durability is required. Furthermore, since PTFE is vulnerable to radiation, unfortunately it cannot be sterilized by radiation.

Consideration may also be given to the use in other applications where sliding properties are required in the presence of water. Specifically, water can be delivered without a loss by reducing the fluid resistance of the inner surface of a pre-filled syringe or of the inner surface of a pipe or tube for delivering water, or by increasing or markedly reducing the contact angle with water. By reducing drag on the inner and outer surfaces of a catheter tube, the catheter tube can be easily inserted into the body and a guide wire can be easily passed through the catheter. Furthermore, drainage of water on wet roads and of snow on snowy roads can be improved by reducing the fluid resistance of the groove surfaces of tires, or by making the contact angle with water large or greatly small. This results in enhanced grip performance and improved hydroplaning performance and therefore better safety. In addition, less adhesion of dirt and dusts can be expected when the sliding resistance of the sidewall surfaces of tires or the walls of buildings is reduced, or when their contact angle with water is increased.

Further advantageous effects can be expected, such as: less pressure loss when water, an aqueous solution or the like is delivered through a diaphragm such as a diaphragm pump or valve; easy sliding of skis or snowboards achieved by enhancing the sliding properties of the sliding surfaces thereof; better noticeability of road signs or signboards achieved by enhancing the sliding properties thereof to allow snow to slide easily on the surface; reduction in water resistance or drag on the outer peripheries of ships and less adhesion of bacteria on the outer peripheries, achieved by reducing the sliding resistance of the outer peripheries or by increasing the contact angle with water; and reduction in water resistance or drag of swimsuits achieved by improving the sliding properties of the thread surfaces thereof.

CITATION LIST

Patent Literature

Patent Literature 1: JP 2004-298220 A
Patent Literature 2: JP 2010-142573 A

SUMMARY OF INVENTION

Technical Problem

The present invention aims to solve the above problems and provide methods for surface-modifying a rubber vulcanizate or a thermoplastic elastomer, which can cost-effectively impart a variety of functions, such as sliding properties or biocompatibility, according to the application. The present invention also aims to provide surface-modified elastic bodies, such as a gasket for syringes at least partially having a surface modified by such a method, and a tire at least partially having a groove surface or sidewall surface modified by such a method.

Solution to Problem

The present invention relates to a method for surface-modifying an object of a rubber vulcanizate or a thermoplastic elastomer, the method including: step 1 of forming polymerization initiation points A on a surface of the object; and step 2 of radically polymerizing a non-functional monomer, starting from the polymerization initiation points A, to grow non-functional polymer chains, and further radically polymerizing a fluorine-containing functional monomer to grow fluorine-containing functional polymer chains.

The step 2 preferably includes radically polymerizing a non-functional monomer, starting from the polymerization initiation points A, to grow non-functional polymer chains, then forming polymerization initiation points B on surfaces of the non-functional polymer chains, and further radically polymerizing a fluorine-containing functional monomer, starting from the polymerization initiation points B, to grow fluorine-containing functional polymer chains.

The step 1 preferably includes adsorbing a photopolymerization initiator onto the surface of the object, optionally followed by irradiation with LED light having a wavelength of 300 to 400 nm, to form polymerization initiation points from the photopolymerization initiator on the surface.

The step 2 preferably includes radically polymerizing a non-functional monomer, starting from the polymerization initiation points A, by irradiation with LED light having a wavelength of 300 to 450 nm to grow non-functional polymer chains, and further radically polymerizing a fluorine-containing functional monomer by irradiation with LED light having a wavelength of 300 to 450 nm to grow fluorine-containing functional polymer chains.

The present invention also relates to a method for surface-modifying an object of a rubber vulcanizate or a thermoplastic elastomer, the method including step I of radically polymerizing a non-functional monomer in the presence of a photopolymerization initiator A on a surface of the object to grow non-functional polymer chains, and further radically polymerizing a fluorine-containing functional monomer in the presence of a photopolymerization initiator B to grow fluorine-containing functional polymer chains.

The step I preferably includes radically polymerizing a non-functional monomer, starting from polymerization initiation points A formed from a photopolymerization initiator A on a surface of the object, to grow non-functional polymer chains, and then radically polymerizing a fluorine-containing functional monomer, starting from polymerization initiation points B formed from a photopolymerization initiator B on surfaces of the non-functional polymer chains, to grow fluorine-containing functional polymer chains.

Preferably, the rubber vulcanizate or thermoplastic elastomer contains an allylic carbon atom which is a carbon atom adjacent to a double bond.

The photopolymerization initiator is preferably at least one of a benzophenone compound and a thioxanthone compound.

In the radical polymerization of the non-functional monomer and/or the fluorine-containing functional monomer in step 2, preferably a reducing agent or an antioxidant is added. The reducing agent or antioxidant is preferably at least one selected from the group consisting of riboflavin, ascorbic acid, α-tocopherol, β-carotene, and uric acid.

Preferably, the surface modification method includes inserting an inert gas into a reaction container and a reaction solution during or before the light irradiation, and polymerizing the monomer in an atmosphere replaced with the inert gas.

Preferably, the non-functional monomer is at least one selected from the group consisting of acrylic acid, acrylic acid esters, acrylic acid alkali metal salts, acrylic acid amine salts, acrylamide, dimethylacrylamide, diethylacrylamide, isopropylacrylamide, hydroxyethylacrylamide, acryloylmorpholine, methoxymethyl acrylate, hydroxyethyl acrylate, methacrylic acid, methacrylic acid esters, methacrylic acid alkali metal salts, methacrylic acid amine salts, methacrylamide, dimethylmethacrylamide, diethylmethacrylamide, isopropylmethacrylamide, hydroxyethylmethacrylamide, methacryloylmorpholine, methoxymethyl methacrylate, hydroxyethyl methacrylate, and acrylonitrile.

Preferably, the fluorine-containing functional monomer is a fluorine-containing (meth)acrylic-modified organic silicon compound that is obtained by an addition reaction of an unsaturated monocarboxylic acid (B) containing a (meth)acrylic group with a fluorine-containing epoxy-modified organic silicon compound (A) represented by the following formula (1):

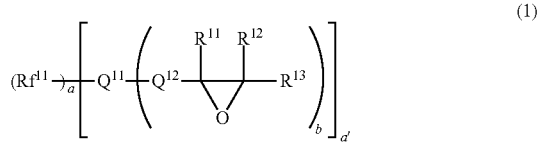
(1)

wherein $Rf^{11}$ represents a monovalent or divalent group having a molecular weight of 100 to 40,000 and containing a fluoroalkyl structure or a fluoropolyether structure; $Q^{11}$ represents a linking group which has a siloxane structure, an unsubstituted or halogen-substituted silalkylene structure, a silarylene structure, or a combination of two or more thereof, each of which contains at least (a+b) silicon atoms and has a valency of (a+b), and $Q^{11}$ may have a cyclic structure; $Q^{12}$ represents a C1-20 divalent hydrocarbon group and $Q^{12}$ may have a cyclic structure and may be interrupted by an ether linkage or an ester linkage; $R^{11}$ to $R^{13}$ each independently represent a hydrogen atom or a C1-10 monovalent hydrocarbon group, provided that a part or all of the hydrogen atoms of $R^{11}$ to $R^{13}$ may be replaced with a halogen atom, and $R^{11}$ and $R^{12}$ may be joined to each other to form a ring together with the carbon atoms to which they are attached; when $Rf^{11}$ is a monovalent group, a' and a represent 1 and an integer of 1 to 6, respectively, and when $Rf^{11}$ is a divalent group, a and a' represent 1 and 2, respectively; and b represents an integer of 1 to 20.

In the formula (1), preferably $Rf^{11}$ contains 1 to 500 repeating units of the following formula:

$$—C_iF_{2i}O—$$

wherein i in each unit independently represents an integer of 1 to 6.

In the formula (1), preferably $Q^{11}$ is represented by the following formula (2):

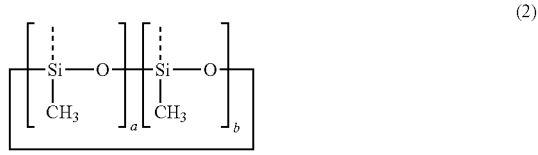
(2)

wherein a and b are as defined in the formula (1); the broken lines represent bonds; the unit having a repeating unit repeated a times is joined to $Rf^{11}$; the unit having a repeating unit repeated b times is joined to a group represented by the following formula:

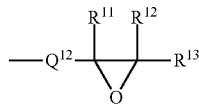

wherein $Q^{12}$ and $R^{11}$ to $R^{13}$ are as defined in the formula (1); the two types of repeating units are randomly arranged; and $Rf^{11}$ is as defined in the formula (1).

In the formula (1), preferably $Rf^{11}$ is represented by the following formula (3):

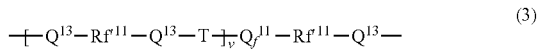
(3)

wherein $Rf^{11}$ represents a divalent perfluoropolyether group having a molecular weight of 300 to 30,000 which may be internally branched; $Q^{13}$ represents a divalent organic group which may contain an oxygen atom, a nitrogen atom, a fluorine atom or a silicon atom and may have a cyclic structure or an unsaturated bond; $Q_f^{11}$ represents $Q^{13}$ or a fluorine atom; T represents a linking group represented by the following formula (4):

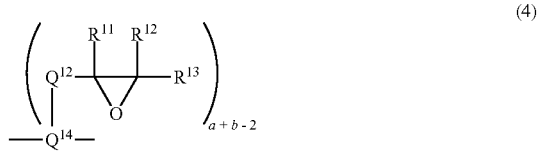
(4)

wherein $R^{11}$ to $R^{13}$, a, and b are as defined in the formula (1), and $Q^{14}$ represents a linking group which has a siloxane structure, an unsubstituted or halogen-substituted silalkylene structure, a silarylene structure, or a combination of two or more thereof, each of which contains at least (a+b) silicon atoms and has a valency of (a+b); and v represents an integer of 0 to 5, provided that v is 0 when $Q_f^{11}$ is a fluorine atom.

Preferably, the fluorine-containing functional monomer is a mixture of a fluorine-containing epoxy-modified organic silicon compound represented by the formula below and a fluorine-containing (meth)acrylic-modified organic silicon compound represented by the formula below:

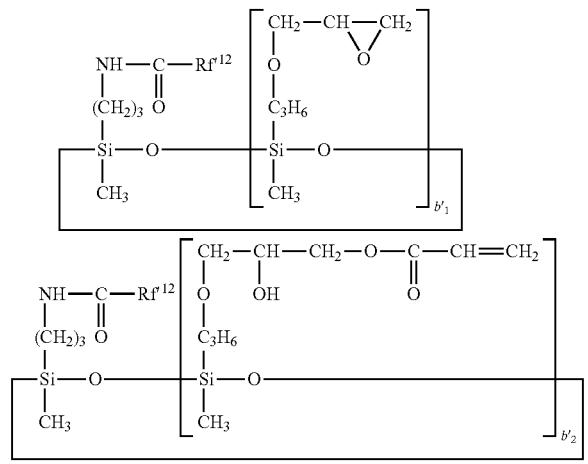

wherein $b'_1+b'_2$ is 2 to 6.5, and $Rf^{12}$ is a group represented by the following formula:

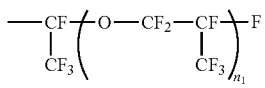

wherein $n_1$ is 2 to 100.

Preferably, the fluorine-containing functional monomer is a polyfunctional (meth)acrylate compound containing three or more fluorine atoms and three or more silicon atoms per molecule, the compound including a cyclic siloxane represented by the following formula:

$$(Rf^{21}R^{21}Sio)(R^4R^{21}SiO)_h$$

wherein $R^{21}$ represents a hydrogen atom, a methyl group, an ethyl group, a propyl group, or a phenyl group; $Rf^{21}$ represents a fluorine-containing organic group; $R^4$ represents a (meth)acrylic group-containing organic group; and $h \geq 2$.

Preferably, $R^4$ is bound to the silicon atom by a Si—O—C bond.

Preferably, $Rf^{21}$ is a group represented by $C_tF_{2t+1}(CH_2)_u^-$ wherein t represents an integer of 1 to 8, and u represents an integer of 2 to 10, or a perfluoropolyether-substituted alkyl group.

Preferably, the fluorine-containing functional monomer has an infrared absorption spectrum having strong absorption peaks at about 1045 $cm^{-1}$ and about 1180 $cm^{-1}$, absorption peaks at about 806 $cm^{-1}$ and about 1720 $cm^{-1}$, a weak absorption peak at about 1532 $cm^{-1}$, and a broad weak absorption peak at about 3350 $cm^{-1}$.

Preferably, the fluorine-containing functional monomer has a $^{13}C$ NMR spectrum in chloroform-d solution having signals at chemical shifts of about 13.01, 14.63, 23.04, 40.13, 50.65, 63.54, 68.97, 73.76, 76.74, 77.06, 77.38, 113.21, 114.11, 116.96, 117.72, 118.47, 128.06, 131.38, 156.46, and 166.02 ppm.

Preferably, the fluorine-containing functional monomer has a $^1H$ NMR spectrum in chloroform-d solution having signals at chemical shifts of about 3.40, 3.41, 3.49, 3.60, 5.26, 5.58, 6.12, 6.14, 6.40, 6.42, and 6.46 ppm.

In the surface modification method, preferably the (liquid) non-functional monomer, the (liquid) fluorine-containing functional monomer, or a solution thereof contains a polymerization inhibitor, and is polymerized in the presence of the polymerization inhibitor. The polymerization inhibitor is preferably 4-methylphenol.

Preferably, a length of the entire polymer chain, including the non-functional polymer chain and the fluorine-containing functional polymer chain, is 10 to 50000 nm.

Preferably, a ratio between a length of the non-functional polymer chain and a length of the fluorine-containing functional polymer chain is 50:50 to 99.9:0.1.

The present invention also relates to a surface-modified elastic body, which is obtained by the above-mentioned method.

The present invention also relates to a surface-modified elastic body, which is obtained by the above-mentioned method, the elastic body being required to have sliding properties, low friction, or low water resistance, in the presence of water or in a dry state.

The present invention also relates to a surface-modified elastic body, which includes a three-dimensional solid, the solid at least partially having a surface modified by the above-mentioned method.

The surface-modified elastic body preferably includes a polymer brush.

The present invention also relates to a gasket for syringes, at least partially having a surface modified by the above-mentioned method.

The present invention also relates to a tire, at least partially having at least one of a groove surface and a sidewall surface which are modified by the above-mentioned method.

Advantageous Effects of Invention

The present invention provides a method for surface-modifying an object of a rubber vulcanizate or a thermoplastic elastomer, the method including: step 1 of forming polymerization initiation points A on the surface of the object; and step 2 of radically polymerizing a non-functional monomer, starting from the polymerization initiation points A, to grow non-functional polymer chains, and further radically polymerizing a fluorine-containing functional monomer to grow fluorine-containing functional polymer chains. According to this method, a polymer layer including fluorine-containing functional polymer chains is formed in the outermost surface of each polymer chain, thereby imparting a desired function. Moreover, the other part of each polymer chain is formed of a polymer layer including non-functional polymer chains. This is economically advantageous.

DESCRIPTION OF EMBODIMENTS

Figure 1:
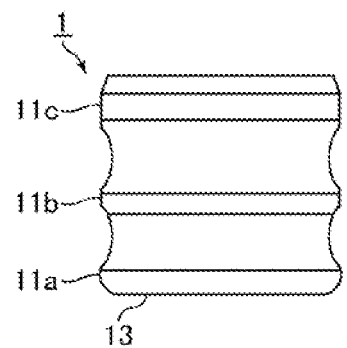
FIG. 1 is an exemplary side view of an embodiment of a gasket for syringes.

The present invention relates to a method for surface-modifying an object of a rubber vulcanizate or a thermoplastic elastomer, the method including: step 1 of forming polymerization initiation points A on the surface of the object; and step 2 of radically polymerizing a non-functional monomer, starting from the polymerization initiation points A, to grow non-functional polymer chains, and further radically polymerizing a fluorine-containing functional monomer to grow fluorine-containing functional polymer chains.

To impart a desired function by forming polymer chains on the surface of a rubber vulcanizate or thermoplastic elastomer which usually has large irregularities, polymer chains need to be formed so that they have a certain height (length) from the surface while functional polymer chains are placed on the top. However, since functional monomers are usually very expensive, the use of such monomers is economically disadvantageous unless the amount of polymer chains formed from the monomers is the minimum required to produce a desired function. In contrast, the present invention provides a surface modification method in which polymer chains are first formed from inexpensive non-functional monomers on the surface of an object of modification to build a certain scaffold, and then a minimum amount of functional polymer chains are built up on the scaffold by polymerizing a fluorine-containing functional monomer, whereby a functional polymer layer is formed on the outermost surface. Thus, the present invention can provide surface-modified elastic bodies that are very cost-effectively imparted with desired functions, such as sliding properties, biocompatibility, or antibacterial properties.

Moreover, since the fluorine-containing functional monomer used in the present invention has low surface free energy, forming functional polymer chains from this monomer on the outermost surface provides a surface having high sliding properties.

The step 1 includes forming polymerization initiation points A on the surface of a vulcanized rubber or a molded thermoplastic elastomer (object of modification).

The rubber vulcanizate or thermoplastic elastomer to be used may suitably contain a carbon atom (allylic carbon atom) adjacent to a double bond.

Examples of rubbers that may be used as the object of modification include diene rubbers such as styrene-butadiene rubber, polybutadiene rubber, polyisoprene rubber, natural rubber, and deproteinized natural rubber; and butyl rubber and halogenated butyl rubber which have a degree of unsaturation of a few percent of isoprene units. The butyl rubber or halogenated butyl rubber, if used, is preferably a rubber cross-linked by triazine because the amount of matter extracted from the rubber vulcanizate is small. In this case, the rubber may contain an acid acceptor. Examples of suitable acid acceptors include hydrotalcite and magnesium carbonate.

In cases where other rubbers are used, sulfur vulcanization is preferably performed. In such cases, compounding agents commonly used for sulfur vulcanization may be added, such as vulcanization accelerators, zinc oxide, filler, and silane coupling agents. Suitable examples of the filler include carbon black, silica, clay, talc, and calcium carbonate.

The vulcanization conditions for the rubber may be appropriately set. The vulcanization temperature for the rubber is preferably 150° C. or higher, more preferably 170° C. or higher, and further preferably 175° C. or higher.

Examples of the thermoplastic elastomer include polymer compounds that have rubber elasticity at room temperature owing to the aggregates of plastic components (hard segments) serving as crosslinking points (e.g., thermoplastic elastomers (TPE) such as styrene-butadiene-styrene copolymers); and polymer compounds having rubber elasticity, obtained by mixing a thermoplastic component and a rubber component and dynamically crosslinking the mixture by a crosslinking agent (e.g., thermoplastic elastomers (TPV) such as polymer alloys containing a styrenic block copolymer or olefinic resin together with a cross-linked rubber component).

Other examples of suitable thermoplastic elastomers include nylon, polyester, polyurethane, polypropylene, and dynamically cross-linked thermoplastic elastomers thereof. Preferred among dynamically cross-linked thermoplastic elastomers are those obtained by dynamically crosslinking halogenated butyl rubber in a thermoplastic elastomer. This thermoplastic elastomer is preferably nylon, polyurethane, polypropylene, SIBS (styrene-isobutylene-styrene block copolymer) or the like.

The polymerization initiation points A may be formed, for example, by adsorbing a photopolymerization initiator A onto the surface of the object of modification. Examples of the photopolymerization initiator A include carbonyl compounds, organic sulfur compounds (e.g. tetraethylthiuram disulfide), persulfides, redox compounds, azo compounds, diazo compounds, halogen compounds, and photoreductive pigments. Preferred among these are carbonyl compounds.

The carbonyl compound as the photopolymerization initiator A is preferably benzophenone or its derivative, and may suitably be a benzophenone compound represented by the following formula:

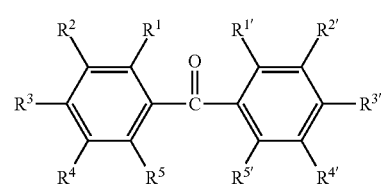

wherein $R^1$ to $R^5$ and $R^{1'}$ to $R^{5'}$ are the same as or different from one another and each represent a hydrogen atom, an alkyl group, a halogen (fluorine, chlorine, bromine, or iodine), a hydroxy group, a primary to tertiary amino group, a mercapto group, or a hydrocarbon group optionally containing an oxygen atom, a nitrogen atom, or a sulfur atom; and any two adjacent groups thereof may be joined to each other to form a cyclic structure together with the carbon atoms to which they are attached.

Specific examples of the benzophenone compound include benzophenone, xanthone, 9-fluorenone, 2,4-dichlorobenzophenone, methyl o-benzoylbenzoate, 4,4'-bis(dimethylamino)benzophenone, and 4,4'-bis(diethylamino)benzophenone. Benzophenone, xanthone, and 9-fluorenone are particularly preferred among these because then good polymer brushes can be formed.

Other examples of suitable benzophenone compounds include fluorobenzophenone compounds, such as 2,3,4,5,6-pentafluorobenzophenone and decafluorobenzophenone represented by the following respective formulas.

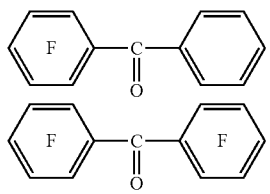

Thioxanthone compounds can also be suitably used as the photopolymerization initiator A because they provide a high polymerization rate and also because they can easily be adsorbed on and/or reacted with rubber or the like. For example, compounds represented by the following formula can be suitably used.

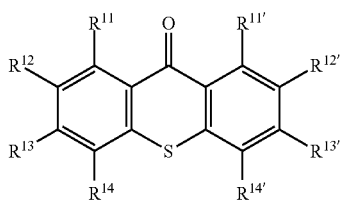

In the formula, $R^{11}$ to $R^{14}$ and $R^{11'}$ to $R^{14'}$ the same as or different from one another and each represent a hydrogen atom, a halogen atom, an alkyl group, a cyclic alkyl group, an aryl group, an alkenyl group, an alkoxy group, or an aryloxy group.

Examples of the thioxanthone compounds represented by the formula include thioxanthone, 2-isopropylthioxanthone, 4-isopropylthioxanthone, 2,3-diethylthioxanthone, 2,4-diethylthioxanthone, 2,4-dichlorothioxanthone, 2-methoxythioxanthone, 1-chloro-4-propoxythioxanthone, 2-cyclohexylthioxanthone, 4-cyclohexylthioxanthone, 2-vinylthioxanthone, 2,4-divinylthioxanthone, 2,4-diphenylthioxanthone, 2-butenyl-4-phenylthioxanthone, 2-methoxythioxanthone, and 2-p-octyloxyphenyl-4-ethylthioxanthone. Preferred among these are the compounds in which one or two, particularly two of the $R^{11}$ to $R^{14}$ and $R^{11'}$ to $R^{14'}$ are substituted with alkyl groups, and more preferred is 2,4-diethylthioxanthone.

The photopolymerization initiator A (e.g. benzophenone compound or thioxanthone compound) may be adsorbed onto the surface of the object of modification by conventionally known methods. In the case of using a benzophenone compound or a thioxanthone compound, for example, the benzophenone or thioxanthone compound is dissolved in an organic solvent to prepare a solution; a surface portion of the object to be modified is treated with this solution so that the compound is adsorbed on the surface; and if necessary, the organic solvent is evaporated off by drying, whereby polymerization initiation points are formed. The surface may be treated by any method that allows the solution of the benzophenone or thioxanthone compound to be brought into contact with the surface of the object of modification. Suitable methods include application or spraying of the benzophenone or thioxanthone compound solution, and immersion into the solution. Moreover, if only a part of the surface needs to be modified, it is sufficient to adsorb the photopolymerization initiator A only onto such a part of the surface. In this case, for example, application or spraying of the solution is suitable. Examples of solvents that can be used include methanol, ethanol, acetone, benzene, toluene, methyl ethyl ketone, ethyl acetate, and THF. Acetone is preferred because it does not swell the object of modification and it can be rapidly dried and evaporated off.

Moreover, it is preferred that after the surface portion to be modified is surface-treated with the benzophenone compound solution or thioxanthone compound solution so that the photopolymerization initiator A is adsorbed thereto, the surface of the object of modification is further irradiated with light so that the polymerization initiator is chemically bonded to the surface. For example, the benzophenone or thioxanthone compound can be fixed on the surface by irradiation with ultraviolet light having a wavelength of 300 to 450 nm (preferably 300 to 400 nm, more preferably 350 to 400 nm). During the step 1 and the fixing, hydrogen is abstracted from the rubber surface, and a carbon atom on the rubber surface is then covalently bonded to the carbon atom in C=O of benzophenone while the abstracted hydrogen is bonded to the oxygen atom in C=O to form C—O—H. Moreover, since this hydrogen abstraction reaction selectively occurs on allylic hydrogen atoms in the object of modification, the rubber preferably contains a butadiene or isoprene unit that contains an allylic hydrogen atom.

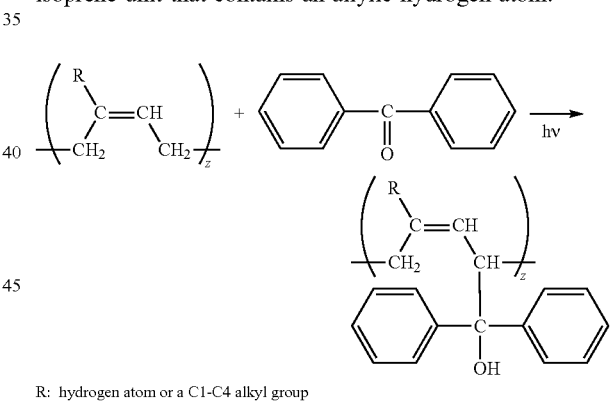

R: hydrogen atom or a C1-C4 alkyl group

In particular, the polymerization initiation points A are preferably formed by treating the surface of the object of modification with the photopolymerization initiator A so that the photopolymerization initiator A is adsorbed on the surface, and then irradiating the treated surface with LED light having a wavelength of 300 to 450 nm. Particularly preferably, after the surface of the object of modification is surface-treated with the benzophenone or thioxanthone compound solution so that the photopolymerization initiator A is adsorbed, the treated surface is further irradiated with LED light having a wavelength of 300 to 450 nm so that the adsorbed photopolymerization initiator A is chemically bonded to the surface. Since light having a wavelength of smaller than 300 nm may cut the molecules in the object of modification to damage the object, light having a wavelength of 300 nm or larger is preferred, and light having a wavewavelength of 355 nm or larger is more preferred in that such light only causes extremely small damage to the object of modification. Also, since light having a wavelength of larger than 450 nm is less likely to activate the polymerization initiator and thus less likely to allow the polymerization reaction to proceed, light having a wavelength of 450 nm or smaller is preferred, and light having a wavelength of 400 nm or smaller is more preferred for greater activation of the polymerization initiator. LED light having a wavelength of 355 to 380 nm is particularly suitable. Although LED light is suitable because it has a narrow band of wavelengths and thus does not have wavelengths other than the center wavelength, a mercury lamp or the like can produce the same effect as that of LED light if light having a wavelength of smaller than 300 nm is blocked using a filter.

The step 2 includes radically polymerizing a non-functional monomer, starting from the polymerization initiation points A, to grow non-functional polymer chains, and further radically polymerizing a fluorine-containing functional monomer to grow fluorine-containing functional polymer chains, and preferably includes radically polymerizing a non-functional monomer, starting from the polymerization initiation points A, to grow non-functional polymer chains, then forming polymerization initiation points B on the surfaces of the non-functional polymer chains, and further radically polymerizing a fluorine-containing functional monomer, starting from the polymerization initiation points B, to grow fluorine-containing functional polymer chains. More specifically, a non-functional monomer is first radically polymerized, starting from the polymerization initiation points A formed in the step 1, to form non-functional polymer chains, and then polymerization initiation points B are optionally formed on the surfaces of the non-functional polymer chains, and further a fluorine-containing functional monomer is radically polymerized, starting from the polymerization initiation points B, to extend the polymer chains so that fluorine-containing functional polymer chains are formed, whereby a surface-modified elastic body having a fluorine-containing functional polymer layer formed on the outermost surface thereof can be prepared.

The non-functional monomer in the step 2 refers to a monomer for forming non-functional polymer chains that do not have functions appropriately chosen according to the application or the like. For example, in the case of imparting such functions as sliding properties, biocompatibility, or antibacterial properties to the object of modification, the non-functional monomer is one which does not impart such functions, and may be appropriately selected in view of economic efficiency or the like. On the other hand, the fluorine-containing functional monomer refers to a monomer capable of forming fluorine-containing functional polymer chains that exhibit a desired function. Examples include fluorine-containing (meth)acrylic-modified organic silicon compounds and cyclic siloxanes, which can impart properties such as sliding properties.

The non-functional monomer may be appropriately selected from the above-mentioned viewpoints, and examples thereof include acrylic acid, acrylic acid esters (e.g. methyl acrylate, ethyl acrylate), acrylic acid alkali metal salts (e.g. sodium acrylate, potassium acrylate), acrylic acid amine salts, acrylamide, dimethylacrylamide, diethylacrylamide, isopropylacrylamide, hydroxyethylacrylamide, acryloylmorpholine, methoxymethyl acrylate, hydroxyethyl acrylate, methacrylic acid, methacrylic acid esters (e.g. methyl methacrylate, ethyl methacrylate), methacrylic acid alkali metal salts (e.g. sodium methacrylate, potassium methacrylate), methacrylic acid amine salts, methacrylamide, dimethylmethacrylamide, diethylmethacrylamide, isopropylmethacrylamide, hydroxyethylmethacrylamide, methacryloylmorpholine, methoxymethyl methacrylate, hydroxyethyl methacrylate, and acrylonitrile. These non-functional monomers may be used alone, or two or more thereof may be used in combination.

The fluorine-containing functional monomer may suitably be, for example, a fluorine-containing (meth)acrylic-modified organic silicon compound that is obtained by an addition reaction of an unsaturated monocarboxylic acid (B) containing a (meth)acrylic group with a fluorine-containing epoxy-modified organic silicon compound (A) represented by the following formula (1):

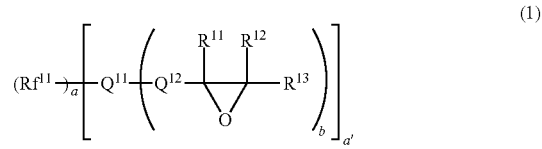

wherein $Rf^{11}$ represents a monovalent or divalent group having a molecular weight of 100 to 40,000 and containing a fluoroalkyl structure or a fluoropolyether structure; $Q^{11}$ represents a linking group which has a siloxane structure, an unsubstituted or halogen-substituted silalkylene structure, a silarylene structure, or a combination of two or more thereof, each of which contains at least (a+b) silicon atoms and has a valency of (a+b), and $Q^{11}$ may have a cyclic structure; $Q^{12}$ represents a C1-20 divalent hydrocarbon group and $Q^{12}$ may have a cyclic structure and may be interrupted by an ether linkage (—O—) or an ester linkage (—COO—); $R^{11}$ to $R^{13}$ each independently represent a hydrogen atom or a C1-10 monovalent hydrocarbon group, provided that a part or all of the hydrogen atoms of $R^{11}$ to $R^{13}$ may be replaced with a halogen atom, and $R^{11}$ and $R^{12}$ may be joined to each other to form a ring together with the carbon atoms to which they are attached; when $Rf^{11}$ is a monovalent group, a' and a represent 1 and an integer of 1 to 6, respectively, and when $Rf^{11}$ is a divalent group, a and a' represent 1 and 2, respectively; and b represents an integer of 1 to 20.

Regarding the fluorine-containing epoxy-modified organic silicon compound (A), specific examples of $Q^{11}$ in the formula (1) include groups having the following structures:

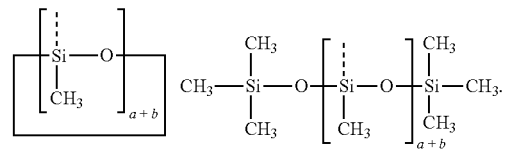

In the formulas, a and b are as defined above and each are preferably an integer of 1 to 4. Moreover, a+b is preferably an integer of 3 to 5. A unit repeated a times and a unit repeated b times are randomly arranged. The bond represented by the broken line in each of the unit repeated a times and the unit repeated b times is attached to $Rf^{11}$ or a group represented by the following formula:

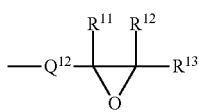

wherein $Q^{12}$ and $R^{11}$ to $R^{13}$ are as defined above.

The divalent hydrocarbon group for $Q^{12}$ in the formula (1) preferably has 2 to 15 carbon atoms. Specific examples of the structure of $Q^{12}$ include —$CH_2CH_2$—, —$CH_2CH(CH_3)$—, and —$CH_2CH_2CH_2OCH_2$—.

The monovalent hydrocarbon group for $R^{11}$ to $R^{13}$ preferably has 1 to 8 carbon atoms. Specific examples of $R^{11}$ to $R^{13}$ include a hydrogen atom, alkyl groups such as a methyl group, an ethyl group, and a propyl group, and cycloalkyl groups such as a cyclopentyl group and a cyclohexyl group.

Examples of groups containing a combination of such $R^{11}$ to $R^{13}$ and $Q^{12}$ in the above formula include the following groups:

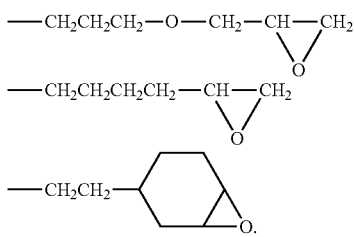

$Rf^{11}$ in the formula (1) preferably has a molecular weight of 500 to 20,000. Moreover, $Rf^{11}$ suitably contains 1 to 500, preferably 2 to 400, more preferably 4 to 200 repeating units of the formula: —$C_iF_{2i}O$— wherein i in each unit independently represents an integer of 1 to 6. In the present invention, molecular weight refers to number average molecular weight calculated from the ratio between the chain end structure and the backbone structure as determined by $^1$H-NMR and $^{19}$F-NMR.

Examples of $Rf^{11}$ in the formula (1) include groups represented by the following formula (3):

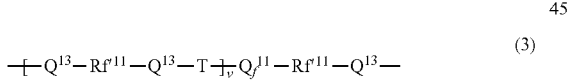
(3)

wherein $Rf^{11}$ represents a divalent perfluoropolyether group having a molecular weight of 300 to 30,000 which may be internally branched; $Q^{13}$ represents a divalent organic group which may contain an oxygen atom, a nitrogen atom, a fluorine atom or a silicon atom and may have a cyclic structure or an unsaturated bond; $Q_f^{11}$ represents $Q^{13}$ or a fluorine atom; T represents a linking group represented by the following formula (4):

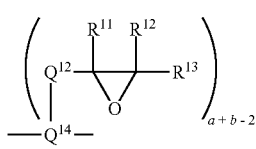
(4)

wherein $R^{11}$ to $R^{13}$, $Q^{12}$, a, and b are as defined in the formula (1), and $Q^{14}$ represents a linking group which has a siloxane structure, an unsubstituted or halogen-substituted silalkylene structure, a silarylene structure, or a combination of two or more thereof, each of which contains at least (a+b) silicon atoms and has a valency of (a+b); and v represents an integer of 0 to 5, provided that v is 0 when $Q_f^{11}$ is a fluorine atom.

$Rf^{11}$ in the formula (3) preferably has a molecular weight of 500 to 20,000. Specific examples of $Rf^{11}$ include divalent perfluoropolyether groups represented by the following formulas:

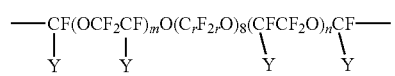

wherein Ys each independently represent a fluorine atom or $CF_3$ group; r represents an integer of 2 to 6; m and n each represent an integer of 0 to 200, preferably 0 to 100, provided that m+n is an integer of 2 to 200, preferably 3 to 150; s represents an integer of 0 to 6; and the repeating units may be randomly linked, and

wherein j represents an integer of 1 to 3, and k represents an integer of 1 to 200, preferably 1 to 60.

Examples of $Q^{13}$ in the formula (3) include the following groups:

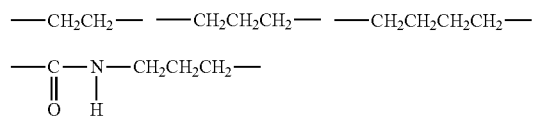

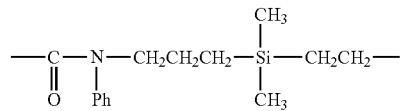

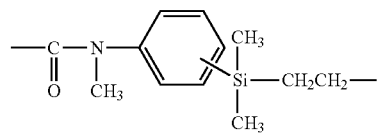

wherein Ph represents a phenyl group.

In the formula (1), when $Rf^{11}$ is a monovalent group, a is preferably an integer of 1 to 3; b is preferably an integer of 1 to 6; and a+b is preferably an integer of 3 to 6.

Specific examples of $Rf^{11}$ in the formula (1) include the following groups:

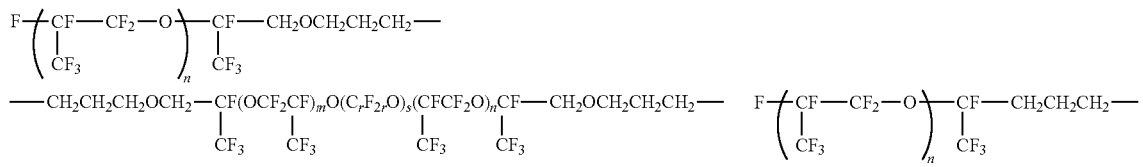

wherein m, n, r, and s are as defined above.

Specific examples of the fluorine-containing epoxy-modified organic silicon compound (A) include the following compounds:

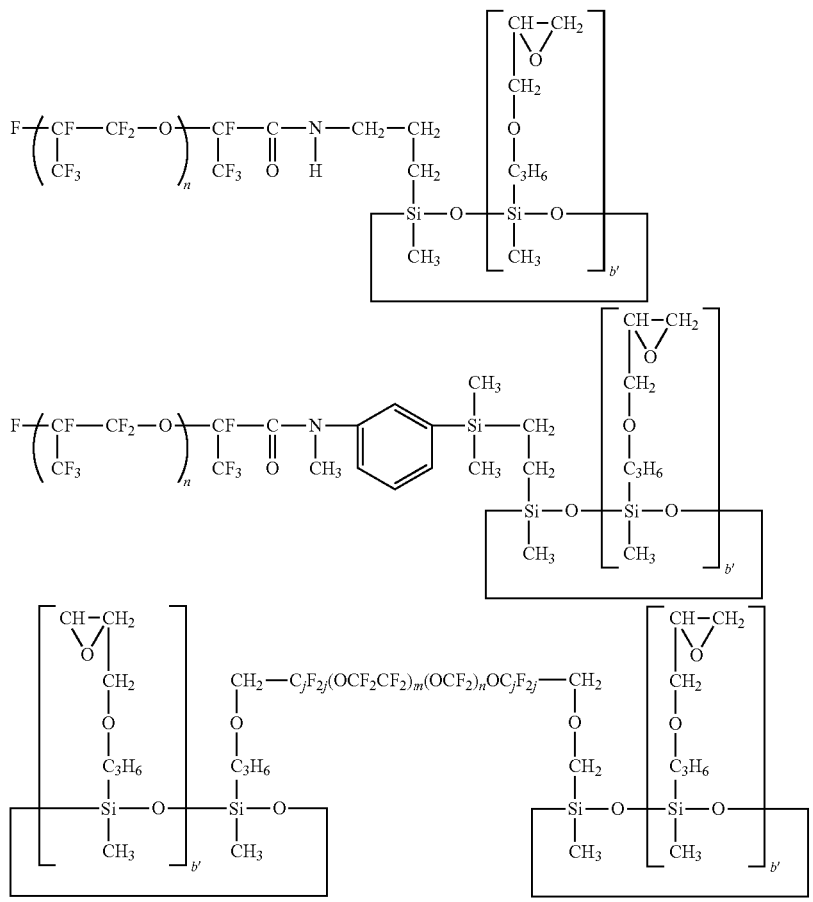

wherein j, m, and n are as defined above, and b' is an integer of 1 to 8.

These fluorine-containing epoxy-modified organic silicon compounds may be used alone or in combination of two or more.

The unsaturated monocarboxylic acid (B) containing a (meth)acrylic group is suitably acrylic acid or methacrylic acid although it may be one in which a part of the hydrogen atoms is halogenated with a halogen atom (e.g. chlorine, fluorine), such as 2-chloroacrylic acid, 2-(trifluoromethyl) acrylic acid, and 2,3,3-trifluoroacrylic acid. Furthermore, these carboxylic acids protected by an allyl group, a silyl group, or the like may optionally be used. The unsaturated monocarboxylic acids may be used alone or in a combination of two or more.

The fluorine-containing (meth)acrylic-modified organic silicon compound in the present invention is obtained by reacting the epoxy group of the fluorine-containing epoxy-modified organic silicon compound (A) with the carboxyl group of the unsaturated monocarboxylic acid (B) containing a (meth)acrylic group by a conventionally known method. Specific examples of the fluorine-containing (meth) acrylic-modified organic silicon compound include the following compounds:

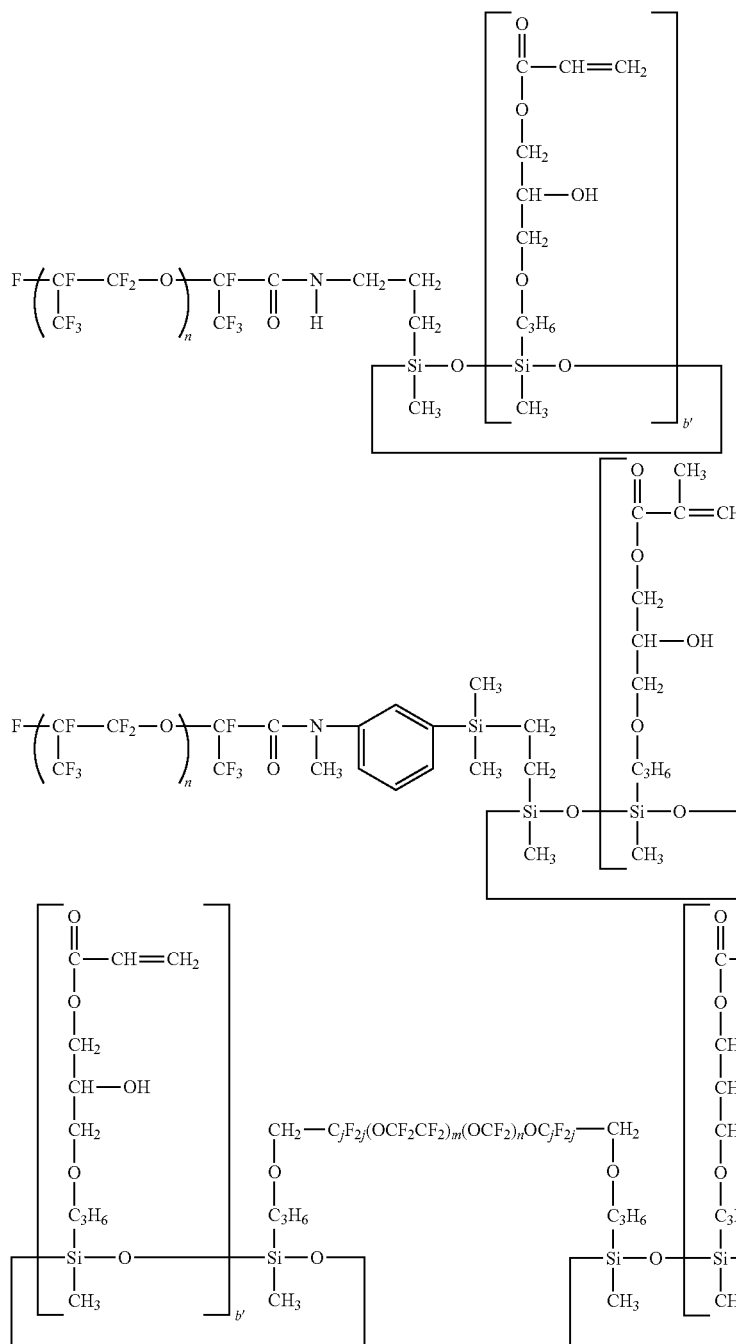

wherein j, m, n, and b' are as defined above.

The fluorine-containing functional monomer in the present invention may suitably be a mixture of a fluorine-containing epoxy-modified organic silicon compound as specifically exemplified above and a fluorine-containing (meth)acrylic-modified organic silicon compound as specifically exemplified above. It is particularly preferably a mixture of a fluorine-containing epoxy-modified organic silicon compound represented by the formula below and a fluorine-containing (meth)acrylic-modified organic silicon compound represented by the formula below:

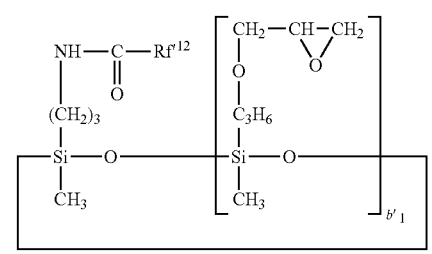

-continued

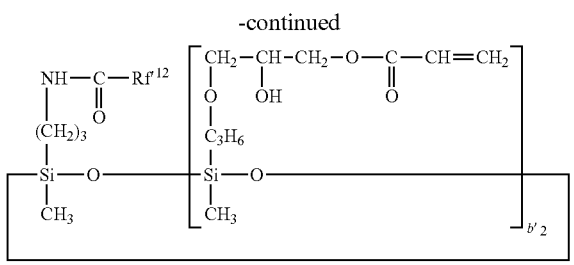

wherein $b'_1+b'_2$ is 2 to 6.5, and $Rf^{12}$ is a group represented by the following formula:

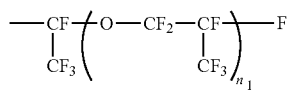

wherein $n_1$ is 2 to 100.

The fluorine-containing functional monomer may also be a polyfunctional (meth)acrylate compound containing three or more fluorine atoms and three or more silicon atoms per molecule, the compound including a cyclic siloxane represented by the following formula:

$(Rf^{21}R^{21}SiO)(R^4R^{21}SiO)_h$ wherein $R^{21}$ represents a hydrogen atom, a methyl group, an ethyl group, a propyl group, or a phenyl group; $Rf^{21}$ represents a fluorine-containing organic group; $R^4$ represents a (meth)acrylic group-containing organic group; and $h \geq 2$.

$Rf^{21}$ in the polyfunctional (meth)acrylate compound may be a group represented by $C_tF_{2t+1}(CH_2)_u$ wherein t represents an integer of 1 to 8, and u represents an integer of 2 to 10, or may be a perfluoropolyether-substituted alkyl group. Specific examples thereof include $CF_3C_2H_4$—, $C_4F_9C_2H_4$—, $C_4F_9C_3H_6$—, $C_8F_{17}C_2H_4$— $C_8F_{17}C_3H_6$—, $C_3F_7C(CF_3)_2C_3H_6$—, $C_3F_7OC(CF_3)$ $FCF_2OCF_2CF_2C_3H_6$—, $C_3F_7OC(CF_3)FCF_2OC(CF_3)$ $FC_3H_6$—, and $CF_3CF_2CF_2OC(CF_3)FCF_2OC(CF_3)$ $FCONHC_3H_6$—.

Specific examples of $R^4$ include $CH_2$=CHCOO—, $CH_2$=C(CH$_3$)COO—, $CH_2$=CHCOOC$_3$H$_6$—, $CH_2$=C(CH$_3$)COOC$_3$H$_6$—, $CH_2$=CHCOOC$_2$H$_4$O—, and $CH_2$=C(CH$_3$)COOC$_2$H$_4$O—. Moreover, $R^4$ is preferably bound to the silicon atom by a Si—O—C bond. The symbol h preferably satisfies $3 \leq h \leq 5$.

The polyfunctional (meth)acrylate compound contains three or more fluorine atoms and three or more silicon atoms per molecule, and preferably contains 3 to 17 fluorine atoms and 3 to 8 silicon atoms.

Specific examples of the polyfunctional (meth)acrylate compound include compounds represented by the following formulas:

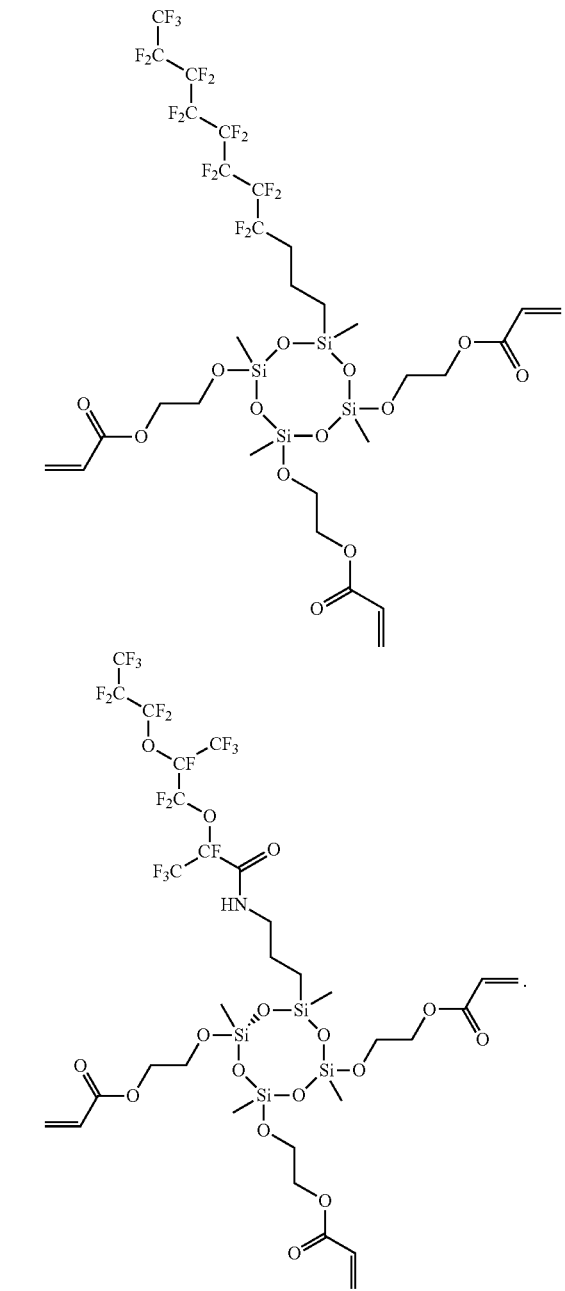

The fluorine-containing functional monomer in the present invention preferably has an infrared absorption spectrum having absorption peaks at about 1045 cm$^{-1}$, about 1180 cm$^{-1}$, about 806 cm$^{-1}$, about 1720 cm$^{-1}$, about 1532 cm$^{-1}$, and about 3350 cm$^{-1}$. In particular, the fluorine-containing functional monomer suitably has an infrared absorption spectrum having strong absorption peaks at about 1045 cm$^{-1}$ and about 1180 cm$^{-1}$, absorption peaks at about 806 cm$^{-1}$ and about 1720 cm$^{-1}$, a weak absorption peak at about 1532 cm$^{-1}$, and a broad weak absorption peak at about 3350 cm$^{-1}$. In this case, fluorine-containing functional polymer chains having excellent properties including excellent sliding properties can be formed.

Moreover, the fluorine-containing functional monomer preferably has a $^{13}C$ NMR spectrum in chloroform-d (deuterated chloroform) solution having signals at chemical shifts of about 13.01, 14.63, 23.04, 40.13, 50.65, 63.54, 68.97, 73.76, 76.74, 77.06, 77.38, 113.21, 114.11, 116.96, 117.72, 118.47, 128.06, 131.38, 156.46, and 166.02 ppm.

The fluorine-containing functional monomer also preferably has a $^1$H NMR spectrum in chloroform-d (deuterated chloroform) solution having signals at chemical shifts of about 3.40, 3.41, 3.49, 3.60, 5.26, 5.58, 6.12, 6.14, 6.40, 6.42, and 6.46 ppm.

In the step 2, the non-functional monomer and the fluorine-containing functional monomer may each be radically polymerized as follows. The (liquid) non-functional monomer or fluorine-containing functional monomer or a solution thereof is applied (sprayed) to the surface of the object of modification to which a benzophenone compound, a thioxanthone compound or the like is adsorbed or covalently bonded, or on the object on which non-functional polymer chains are formed. Alternatively, the object of modification or the object on which non-functional polymer chains are formed is immersed in the (liquid) non-functional monomer or fluorine-containing functional monomer or a solution thereof. Then, the object of modification is irradiated with light, such as ultraviolet light, to allow the radical polymerization (photoradical polymerization) of the corresponding monomer to proceed. Thus, non-functional polymer chains and fluorine-containing functional polymer chains can be grown in said order on the surface of the object of modification. As another method, after the application, the surface may be covered with a transparent sheet of glass, PET, polycarbonate, or the like, followed by irradiating the covered surface with light (e.g. ultraviolet light) to allow the radical polymerization (photoradical polymerization) of the corresponding monomer to proceed. Thus, non-functional polymer chains and fluorine-containing functional polymer chains can be grown in said order on the surface of the object of modification.

In the step 2, radical polymerization (photoradical polymerization) is preferably allowed to proceed by irradiating the non-functional monomer or fluorine-containing functional monomer to which a reducing agent or antioxidant is added, with light. This is desirable because the reducing agent or antioxidant scavenges oxygen in the system. The monomer to which a reducing agent or antioxidant is added may either be one in which these components are mixed with or separated from each other. Moreover, after the object of modification obtained in the step 1 is brought into contact with the non-functional monomer, or after the object on which non-functional polymer chains are formed is brought into contact with the fluorine-containing functional monomer, a reducing agent or antioxidant may be further added thereto. Alternatively, these components may be mixed together in advance before the material mixture is brought into contact with the object of modification or the object on which non-functional polymer chains are formed.

Specifically, non-functional polymer chains and fluorine-containing functional polymer chains may be formed in said order by the radical polymerization of the respective monomers as follows. For example, a step is performed in which light is irradiated after the object of modification obtained in the step 1, on the surface of which polymerization initiation points A are formed from the photopolymerization initiator A, is brought into contact (e.g. immersion, application) with the (liquid) non-functional monomer or a solution thereof, to which a solution of a reducing agent or antioxidant is added, or after the object of modification is brought into contact with the (liquid) non-functional monomer or a solution thereof and then a solution of a reducing agent or antioxidant is put thereon. Then, the object on which non-functional polymer chains are formed is subjected to a similar step using the (liquid) fluorine-containing functional monomer or a solution thereof, and a solution of a reducing agent or antioxidant.

In the case of using, for example, a fluorine-containing functional monomer that has a specific gravity of more than 1 and is not miscible with water, a solution of a reducing agent or antioxidant is located over the (liquid) radically polymerizable monomer or a solution thereof while being separated therefrom.

The reducing agent or antioxidant is not particularly limited and may be any appropriate compound that functions as such an agent. Examples thereof include vitamins A such as retinol, dehydroretinol, retinol acetate, retinol palmitate, retinal, retinoic acid, and vitamin A oil, and derivatives or salts thereof; carotenoids such as α-carotene, β-carotene, γ-carotene, cryptoxanthin, astaxanthin, and fucoxanthin, and derivatives thereof; vitamins B such as pyridoxine, pyridoxal, pyridoxal-5-phosphate, and pyridoxamine, and derivatives or salts thereof; vitamins C such as ascorbic acid, sodium ascorbate, ascorbyl stearate, ascorbyl palmitate, ascorbyl dipalmitate, and magnesium ascorbyl phosphate, and derivatives or salts thereof; vitamins D such as ergocalciferol, cholecalciferol, and 1,2,5-dihydroxy-cholecalciferol, and derivatives or salts thereof; vitamins E such as α-tocopherol, β-tocopherol, γ-tocopherol, δ-tocopherol, α-tocotrienol, β-tocotrienol, γ-tocotrienol, δ-tocotrienol, tocopherol acetate, and tocopherol nicotinate, and derivatives or salts thereof; trolox and derivatives or salts thereof; dihydroxytoluene, butylhydroxytoluene, butylhydroxyanisole, dibutylhydroxytoluene, α-lipoic acid, dehydrolipoic acid, and glutathione, and derivatives or salts thereof; uric acid, erythorbic acid, and erythorbates such as sodium erythorbate, and derivatives or salts thereof; gallic acid and gallates such as propyl gallate, and derivatives or salts thereof; rutin and rutins such as α-glycosylrutin, and derivatives or salts thereof; tryptophan and derivatives or salts thereof; histidine and derivatives or salts thereof; cysteine derivatives or salts such as N-acetylcysteine, N-acetylhomocysteine, N-octanoylcysteine, and N-acetylcysteine methyl ester; cystine derivatives or salts such as N,N'-diacetylcystine dimethyl ester, N,N'-dioctanoylcystine dimethyl ester, and N,N'-dioctanoylhomocystine dimethyl ester; carnosine and derivatives or salts thereof; homocarnosine and derivatives or salts thereof; anserine and derivatives or salts thereof; carcinine and derivatives or salts thereof; dipeptide or tripeptide derivatives or salts containing histidine and/or tryptophan and/or histamine; flavonoids such as flavanone, flavone, anthocyanin, anthocyanidin, flavonol, quercetin, quercitrin, myricetin, fisetin, hamamelitannin, catechin, epicatechin, gallocatechin, epigallocatechin, epicatechin gallate, and epigallocatechin gallate; tannic acid, caffeic acid, ferulic acid, protocatechuic acid, calcone, oryzanol, carnosol, sesamol, sesamine, sesamolin, zingerone, curcumin, tetrahydrocurcumin, clovamide, deoxyclovamide, shogaol, capsaicine, vanillylamide, ellagic acid, bromphenol, flavoglaucin, melanoidin, riboflavin, riboflavin butyrate, flavin mononucleotide, flavin adenine nucleotide, ubiquinone, ubiquinol, mannitol, bilirubin, cholesterol, ebselen, selenomethionine, ceruloplasmin, transferrin, lactoferrin, albumin, superoxide dismutase, catalase, glutathione peroxidase, metallothionein, and O-phosphono-pyridoxylidene rhodamine. These may be used alone or in combination of two or more.

Riboflavin, ascorbic acid, α-tocopherol, β-carotene, and uric acid are preferred among these, and riboflavin and ascorbic acid are particularly preferred, because of their high oxygen scavenging capability.

In the case of using a solution of a reducing agent or antioxidant, the concentration of the reducing agent or antioxidant is preferably $10^{-4}$ to 1% by mass, and more preferably $10^{-3}$ to 0.1% by mass.

Moreover, the amounts of the radically polymerizable monomers may be appropriately set depending on, for example, the length of polymer chains formed, or the properties provided by the chains. Also, the amount of the reducing agent or antioxidant may be appropriately set, for example, in view of the capability of scavenging oxygen in the system.

The solvent for application (spraying), the method for application (spraying), the method for immersion, the conditions for irradiation, and the like may be conventionally known materials or methods. The solutions of the radically polymerizable monomers may each be an aqueous solution, or a solution prepared by dissolving the monomer in an organic solvent that does not dissolve the photopolymerization initiator (e.g. benzophenone compound or thioxanthone compound) to be used. Furthermore, each of the (liquid) radically polymerizable monomers, or a solution thereof may contain a known polymerization inhibitor such as 4-methylphenol.

In the present invention, the radical polymerization of the non-functional monomer or fluorine-containing functional monomer is allowed to proceed by light irradiation after the application of the (liquid) monomer or a solution thereof or after the immersion in the monomer or a solution thereof. Here, UV light sources with an emission wavelength mainly in the ultraviolet region, such as high-pressure mercury lamps, metal halide lamps, and LED lamps, can be suitably used. The light dose may be appropriately determined in consideration of polymerization time and uniformity of reaction. In order to prevent polymerization inhibition due to active gas such as oxygen in the reaction container, it is also preferable to remove oxygen from the reaction container and the reaction solution during or before the light irradiation. Thus, for example, a method may appropriately be employed in which an inert gas, such as nitrogen gas or argon gas, is inserted into the reaction container and the reaction solution to discharge active gas such as oxygen from the reaction system and replace the atmosphere in the reaction system with the inert gas. Also, in order to prevent reaction inhibition due to oxygen or the like, for example, a measure may appropriately be taken in which a UV light source is disposed so that no air layer (oxygen content: 15% or higher) exists between the reaction container made of glass, plastics or the like, and the reaction solution or the object of modification.

In the case of irradiation with ultraviolet light, the ultraviolet light preferably has a wavelength of 300 to 450 nm, more preferably 300 to 400 nm. This allows good polymer chains to be formed on the surface of the object of modification. The light source may be a high-pressure mercury lamp, an LED with a center wavelength of 365 nm, an LED with a center wavelength of 375 nm, or the like. In particular, preferred is irradiation with LED light having a wavelength of 300 to 400 nm, more preferably LED light having a wavelength of 355 to 380 nm. For example, an LED with a center wavelength of 365 nm, which is close to the excitation wavelength (366 nm) of benzophenone, is particularly preferred in view of efficiency.

In the case where the step 2 is carried out by radically polymerizing a non-functional monomer, starting from the polymerization initiation points A, to grow non-functional polymer chains, then forming polymerization initiation points B on the surfaces of the non-functional polymer chains, and further radically polymerizing a fluorine-containing functional monomer, starting from the polymerization initiation points B, to grow fluorine-containing functional polymer chains, the polymerization initiation points B may be formed by the same techniques as those mentioned in the step 1, such as by additionally adsorbing a photopolymerization initiator B onto the surface of the formed non-functional polymer chains, optionally followed by chemically bonding the photopolymerization initiator B to the surface. The photopolymerization initiator B may be as mentioned for the photopolymerization initiator A.

The present invention also relates to a method for surface-modifying an object of a rubber vulcanizate or a thermoplastic elastomer, the method including a step I of radically polymerizing a non-functional monomer in the presence of a photopolymerization initiator A on the surface of the object to grow non-functional polymer chains, and further radically polymerizing a fluorine-containing functional monomer in the presence of a photopolymerization initiator B to grow fluorine-containing functional polymer chains. More specifically, a non-functional monomer is radically polymerized using a photopolymerization initiator A as initiator to form non-functional polymer chains, and then a fluorine-containing functional monomer is further radically polymerized using a photopolymerization initiator B as initiator on the non-functional polymer chains to extend the polymer chains so that fluorine-containing functional polymer chains are formed, whereby a surface-modified elastic body having a fluorine-containing functional polymer layer formed on the outermost surface thereof can be prepared.

The step I preferably includes radically polymerizing a non-functional monomer, starting from polymerization initiation points A formed from a photopolymerization initiator A on the surface of the object of modification, to grow non-functional polymer chains, and then radically polymerizing a fluorine-containing functional monomer, starting from polymerization initiation points B formed from a photopolymerization initiator B on the surfaces of the non-functional polymer chains, to grow fluorine-containing functional polymer chains. For example, the step I may be carried out by contacting a photopolymerization initiator A and a non-functional monomer with the surface of the object of modification, followed by irradiation with LED light having a wavelength of 300 to 450 nm, to form polymerization initiation points A from the photopolymerization initiator A while radically polymerizing the non-functional monomer, starting from the polymerization initiation points A, to grow non-functional polymer chains; and then contacting a photopolymerization initiator B and a functional monomer with the surfaces of the non-functional polymer chains, followed by irradiation with LED light having a wavelength of 300 to 450 nm, to form polymerization initiation points B from the photopolymerization initiator B while radically polymerizing the fluorine-containing functional monomer, starting from the polymerization initiation points B, to grow fluorine-containing functional polymer chains.

In the step I, the non-functional monomer and the fluorine-containing functional monomer may each be radically polymerized as follows. The (liquid) non-functional monomer or fluorine-containing functional monomer or a solution thereof, which contains a photopolymerization initiator A or B (e.g. a benzophenone compound or thioxanthone compound) is applied (sprayed) to the surface of the object of modification or on the object on which non-functional polymer chains are formed. Alternatively, the object of modification or the object on which non-functional polymer chains are formed is immersed in the (liquid) non-functional monomer or fluorine-containing functional monomer or a solution thereof, which contains a photopolymerization initiator A or B. Then, the object of modification is irradiated with light, such as ultraviolet light, to allow the radical polymerization (photoradical polymerization) of the corresponding monomer to proceed. Thus, non-functional polymer chains and fluorine-containing functional polymer chains can be grown in said order on the surface of the object of modification. As another method, for example the surface may be covered with the above-mentioned transparent sheet of glass, PET, polycarbonate, or the like, followed by irradiating the covered surface with light, such as ultraviolet light. Here, a reducing agent or antioxidant may be added similarly as above. The solvent for application (spraying), the method for application (spraying), the method for immersion, the conditions for irradiation, and the like may be materials and methods as mentioned above.

Moreover, the polymer chains including fluorine-containing functional polymer chains formed in the step 2 or the step I provide excellent sliding properties and durability while maintaining good sealing properties. The formed polymer chains preferably each have a polymerization degree of 20 to 200000, more preferably 350 to 50000.

The length of the entire polymer chain, including the non-functional polymer chain and the fluorine-containing functional polymer chain, formed in the step 2 or the step I is preferably 10 to 50000 nm, and more preferably 100 to 50000 nm. A length shorter than 10 nm tends not to provide good sliding properties. A length longer than 50000 nm is unlikely to provide even better sliding properties but tends to drive up the cost of raw materials due to the use of the expensive monomer. In addition, surface patterns generated by the surface treatment tend to be visible to the naked eyes and thereby spoil the appearance and decrease sealing properties.

Regarding the entire polymer chain formed in the step 2 or the step I, the ratio between the length of the non-functional polymer chain and the length of the fluorine-containing functional polymer chain [(length of non-functional polymer chain):(length of fluorine-containing functional polymer chain)] is preferably 50:50 to 99.9:0.1, more preferably 90:10 to 99.5:0.5. If the length of the fluorine-containing functional polymer chain is shorter than 1%, desired functions may not be imparted. If it exceeds 50%, there tends to be an economic disadvantage.

In the step 2 or the step I, two or more types of non-functional monomers may simultaneously be radically polymerized starting from the polymerization initiation points B, and two or more types of fluorine-containing functional monomers may simultaneously be radically polymerized. Moreover, two or more layers of the non-functional polymer chains or of the fluorine-containing functional polymer chains may be stacked. Furthermore, multiple types of polymer chains may be grown on the surface of the object of modification. In the surface modification method of the present invention, the polymer chains may be cross-linked to one another. In this case, the polymer chains may be cross-linked to one another by ionic crosslinking, crosslinking by a hydrophilic group containing an oxygen atom, or crosslinking by a halogen group (e.g. iodine).

The surface modification method can be applied to a rubber vulcanizate or a thermoplastic elastomer to prepare a surface-modified elastic body. For example, a surface-modified elastic body excellent in sliding properties in the presence of water or in a dry state can be prepared. This surface-modified elastic body is also excellent in that it has low friction and low water resistance or drag. Moreover, the method can be applied to at least a part of a three-dimensional solid (e.g. elastic body) to prepare a surface-modified elastic body having modified quality. Furthermore, preferred examples of such surface-modified elastic bodies include polymer brushes. Polymer brush herein means an assembly of graft polymer molecules obtained by the "grafting from" approach by surface-initiated living radical polymerization. The graft chains are preferably oriented in a direction substantially vertical to the surface of the object of modification because, in such a case, entropy is reduced and thus the molecular mobility of the graft chains is reduced, thereby contributing to sliding properties. Moreover, semidilute brushes and concentrated brushes which have a brush density of 0.01 chains/nm$^2$ or higher are preferred.

Furthermore, the surface modification method can be applied to a rubber vulcanizate or a thermoplastic elastomer to prepare a gasket for syringes at least partially having a modified surface. The modification is preferably performed at least on the sliding portion of the gasket surface, or may be performed on the entire surface.

FIG. 1 is an exemplary side view of an embodiment of the gasket for syringes. A gasket 1 shown in FIG. 1 has three circular protruding portions 11a, 11b and 11c each of which continuously protrudes along the circumferential direction on the outer periphery that is to be in contact with the inner periphery of a syringe barrel. Examples of the portions of the gasket 1 to which the surface modification is applied include (1) the surfaces of protruding portions to be in contact with a syringe barrel, such as the circular protruding portions 11a, 11b and 11c; (2) the entire side surface including the circular protruding portions 11a, 11b and 11c; and (3) both the entire side surface and a bottom surface 13.

Furthermore, if the method is applied to the grooves in the tread of a tire for use on vehicles such as passenger cars to form a polymer brush on the grooves, the fluid resistance of the groove surface on wet or snowy roads is reduced, and the contact angle with water is increased. Thus, the abilities to remove and drain water or snow are enhanced, resulting in improved grip performance.

Figure 2:
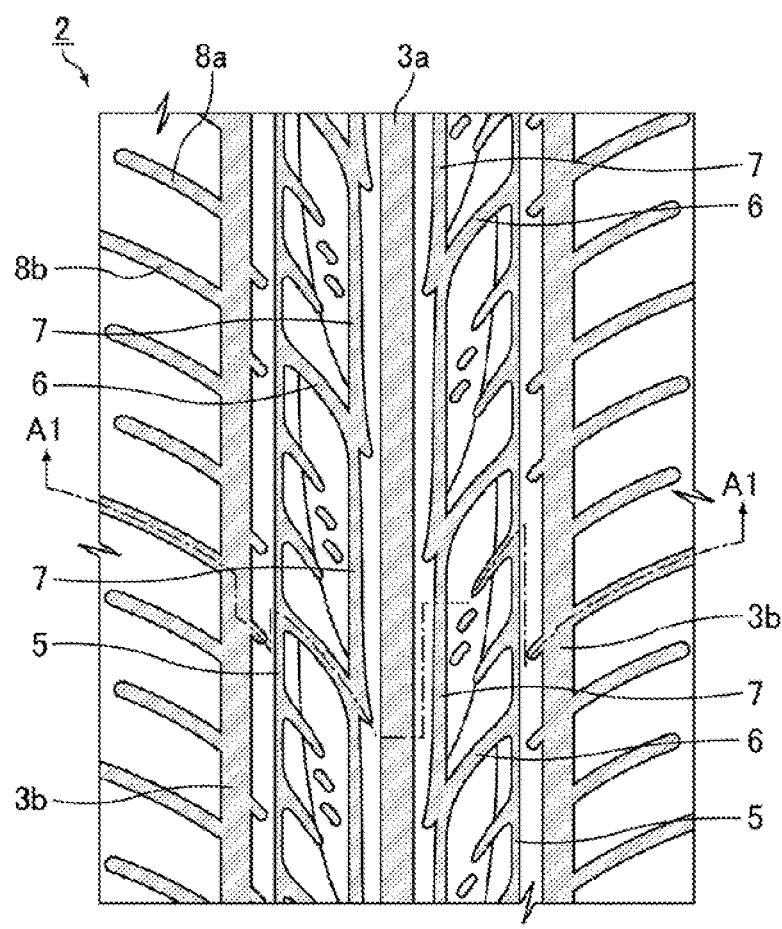
FIG. 2 is an exemplary development view of the tread portion of a pneumatic tire (the whole tire is not shown).
Figure 3:
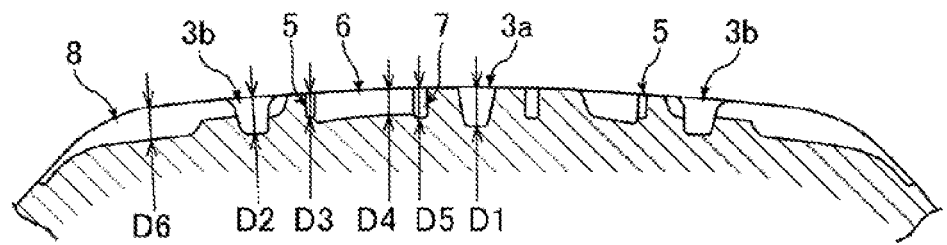
FIG. 3 is an exemplary A1-A1 cross-sectional view of FIG. 2.
Figure 4:
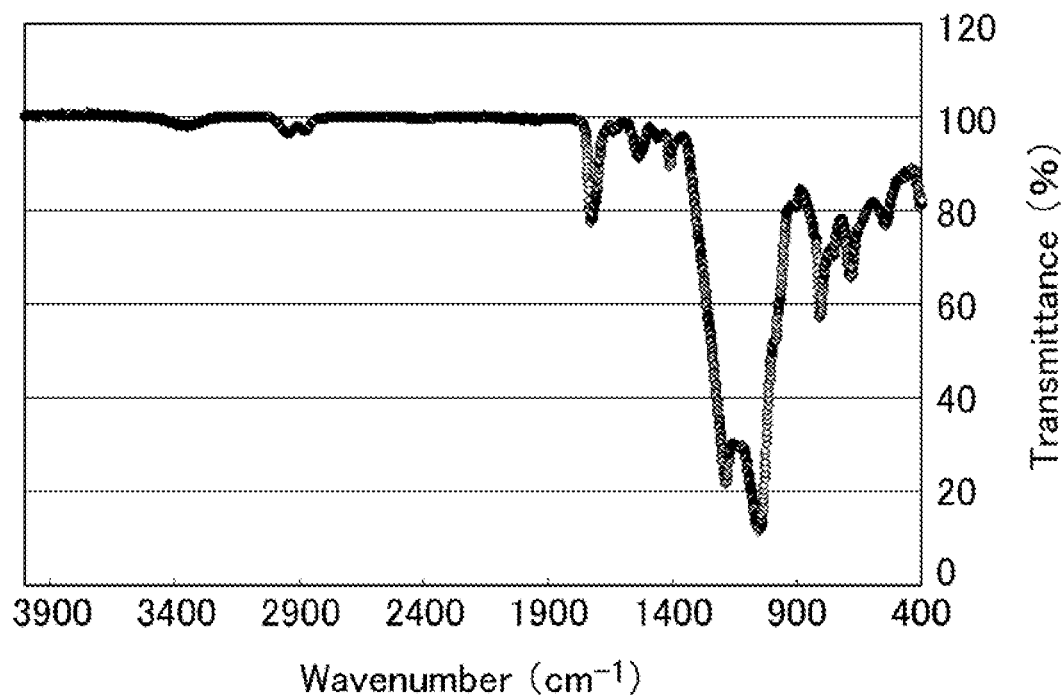
FIG. 4 is an infrared absorption spectrum of a fluorine-containing functional monomer liquid (KY-1203, produced by Shin-Etsu Chemical Co., Ltd.) used in Example 1.
Figure 5:
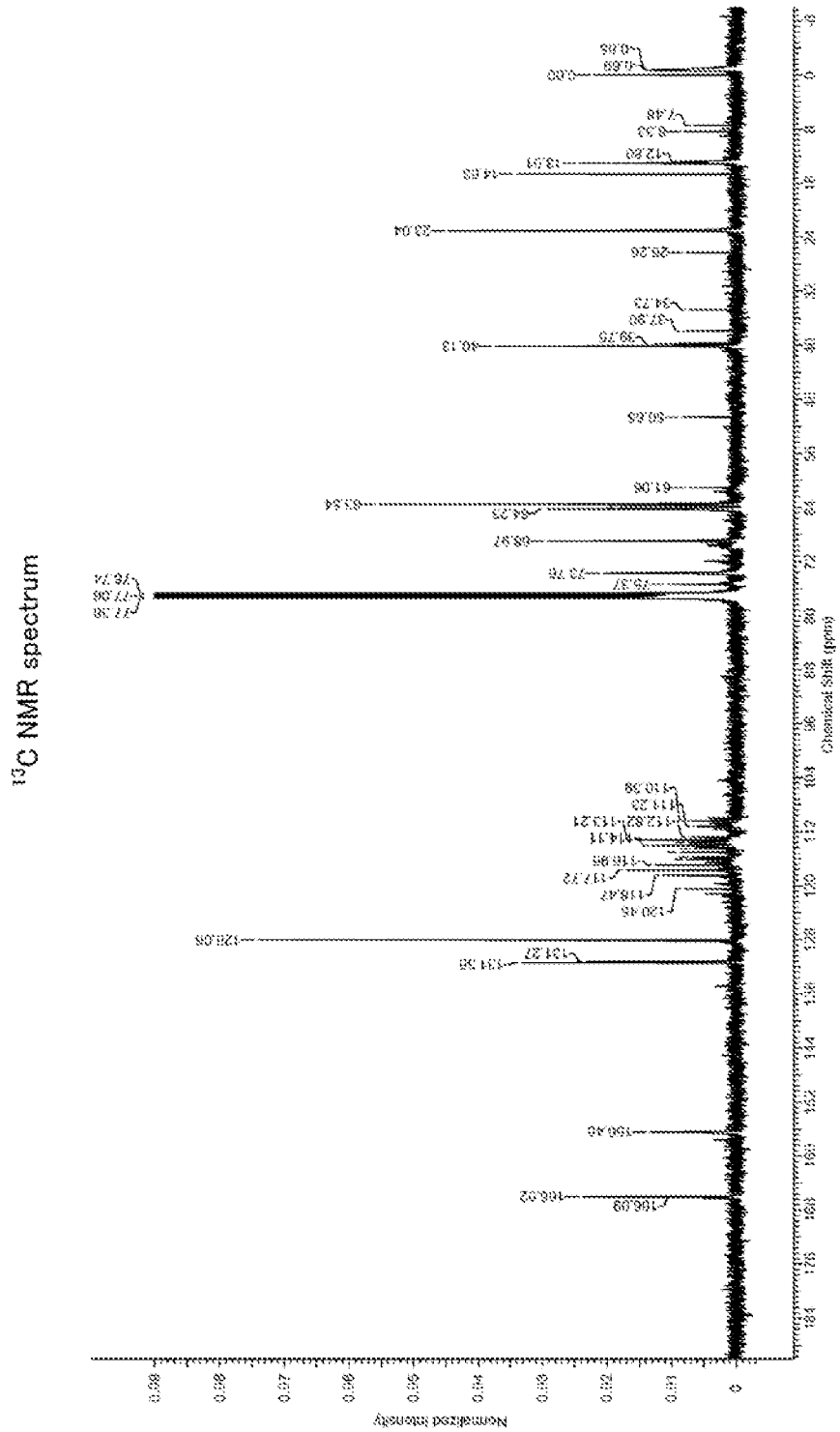
FIG. 5 is a $^{13}$C-NMR spectrum of a fluorine-containing functional monomer liquid (KY-1203, produced by Shin-Etsu Chemical Co., Ltd.) used in Example 1.
Figure 6:
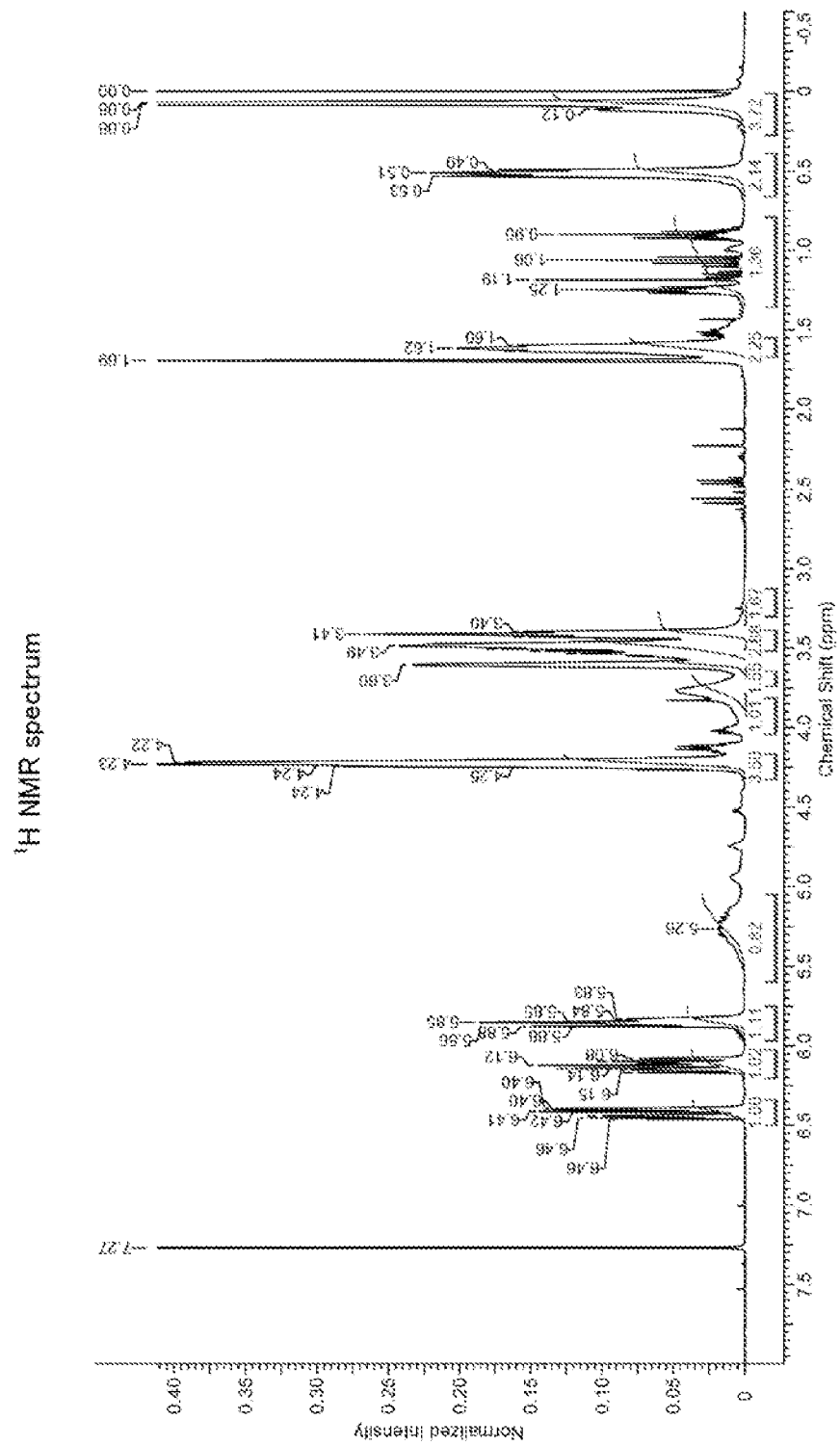
FIG. 6 is a $^1$H-NMR spectrum of a fluorine-containing functional monomer liquid (KY-1203, produced by Shin-Etsu Chemical Co., Ltd.) used in Example 1.

FIG. 2 is an exemplary development view of a tread portion 2 of a pneumatic tire (the whole tire is not shown). FIG. 3 is an exemplary A1-A1 cross-sectional view of FIG. 2.

In FIGS. 2 and 3, a longitudinal center groove 3a (groove depth D1) and longitudinal shoulder grooves 3b (groove depth D2) are straight grooves linearly extending in the circumferential direction of the tire. Such straight grooves can contribute to low drainage resistance and high drainage performance during straight travelling.

The pneumatic tire also has fine grooves 5 (groove depth D3) extending in the tire circumferential direction on the side of the longitudinal shoulder groove 3b; beveled intermediate grooves 6 (groove depth D4) extending with an inclination from the fine groove 5 toward the longitudinal center groove 3a; connecting grooves 7 (groove depth D5) located inward of the fine grooves 5 in the axis direction of the tire and connecting the beveled intermediate grooves 6 next to one another in the circumferential direction of the tire; lateral shoulder grooves 8, 8a and 8b (groove depth D6) extending from the longitudinal shoulder groove 3b toward the outside of the tire; and the like. These grooves can also contribute to drainage performance. If the method is applied to these grooves, the above-mentioned effects can be achieved. Moreover, if the method is applied to the sidewall surface, an effect of reducing adhesion of dirt and dust to the surface can be expected.

EXAMPLES

The following will describe the present invention in more detail, referring to, though not limited to, examples.

Example 1

A chlorobutyl rubber (degree of unsaturation: 1 to 2%) containing isoprene units was cross-linked by triazine to prepare a vulcanized rubber gasket (vulcanized at 180° C. for 10 minutes), which was then immersed in a solution of benzophenone in acetone (3 wt %) so that benzophenone was adsorbed onto the surface of the rubber vulcanizate, followed by drying. Then the surface of the vulcanized rubber gasket was irradiated with LED-UV light having a wavelength of 365 nm for 10 minutes to chemically bond benzophenone to the surface. Thereafter, the surface was washed with acetone to remove unreacted benzophenone. The resulting rubber vulcanizate was taken out and dried.

The dried vulcanized rubber gasket was immersed in an aqueous acrylic acid solution (2.5 M, 18 g of acrylic acid dissolved in 100 mL of water) in a glass reaction container. Then the gasket was irradiated with LED-UV light having a wavelength of 365 nm for one hour to cause radical polymerization and thereby grow non-functional polymer chains on the surface of the rubber. Then, the surface was washed with water and dried.

Next, a fluorine-containing functional monomer solution (KY-1203 produced by Shin-Etsu Chemical Co., Ltd., a mixture of a fluorine-containing epoxy-modified organic silicon compound represented by the formula below and a fluorine-containing (meth)acrylic-modified organic silicon compound represented by the formula below) was applied to the surface of the vulcanized rubber gasket where polyacrylic acid was grown. Thereafter, the surface was irradiated with LED-UV light having a wavelength of 365 nm for 15 minutes in an argon gas atmosphere to cause radical polymerization and thereby further grow fluorine-containing functional polymer chains on the polyacrylic acid chains (non-functional polymer chains). In this manner, a surface-modified elastic body (a polymer brush layer on the surface) was obtained,

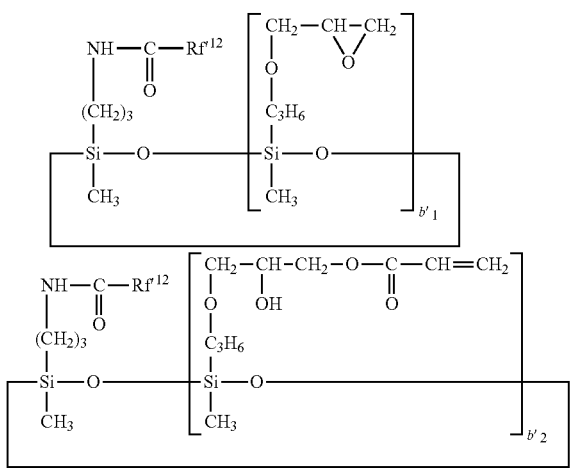

In the formulas, $b'_1 + b'_2$ is 2 to 6.5, and $Rf^{12}$ is a group represented by the following formula:

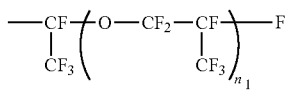

wherein $n_1$ is 2 to 100.

Example 2

A surface-modified elastic body (a polymer brush layer on the surface) was obtained as in Example 1, except that the polymerization time (time of LED-UV light irradiation) of the fluorine-containing functional monomer solution was changed to 30 minutes.

Example 3

A chlorobutyl rubber (degree of unsaturation: 1 to 2%) containing isoprene units was cross-linked by triazine to prepare a vulcanized rubber gasket (vulcanized at 180° C. for 10 minutes), which was then immersed in a solution of benzophenone in acetone (3 wt %) so that benzophenone was adsorbed onto the surface of the rubber vulcanizate, followed by drying.

The dried vulcanized rubber gasket was immersed in an aqueous acrylic acid solution (2.5 M, 18 g of acrylic acid dissolved in 100 mL of water) in a glass reaction container. Then the gasket was irradiated with LED-UV light having a wavelength of 365 nm for 30 minutes to cause radical polymerization and thereby grow non-functional polymer chains on the surface of the rubber. Then, the surface was washed with water and dried.

Next, the dried vulcanized rubber gasket was immersed in a solution of benzophenone in acetone (3 wt %) so that benzophenone was adsorbed onto the surface of the polyacrylic acid, followed by drying. Further, a fluorine-containing functional monomer solution (KY-1203 produced by Shin-Etsu Chemical Co., Ltd.) was applied to the surface of the vulcanized rubber gasket where benzophenone was adsorbed on the polyacrylic acid surface. Thereafter, the surface was irradiated with LED-UV light having a wavelength of 365 nm for 15 minutes in an argon gas atmosphere to cause radical polymerization and thereby further grow fluorine-containing functional polymer chains on the polyacrylic acid chains (non-functional polymer chains). In this manner, a surface-modified elastic body (a polymer brush layer on the surface) was obtained.

Example 4

A chlorobutyl rubber (degree of unsaturation: 1 to 2%) containing isoprene units was cross-linked by triazine to prepare a vulcanized rubber gasket (vulcanized at 180° C. for 10 minutes), which was then immersed in a solution of benzophenone in acetone (1 wt %) so that benzophenone was adsorbed onto the surface of the rubber vulcanizate, followed by drying.

The dried vulcanized rubber gasket was immersed in an aqueous acrylic acid solution (2.5 M, 18 g of acrylic acid dissolved in 100 mL of water) in a glass reaction container. Then the gasket was irradiated with LED-UV light having a wavelength of 365 nm for 30 minutes to cause radical polymerization and thereby grow non-functional polymer chains on the surface of the rubber. Then, the surface was washed with water and dried.

Next, the dried vulcanized rubber gasket was immersed in a solution of benzophenone in acetone (1 wt %) so that benzophenone was adsorbed onto the surface of the polyacrylic acid, followed by drying. Further, a fluorine-containing functional monomer solution (KY-1203 produced by Shin-Etsu Chemical Co., Ltd.) was applied to the surface of the vulcanized rubber gasket where benzophenone was adsorbed onto the polyacrylic acid surface. Thereafter, the surface was irradiated with LED-UV light having a wavelength of 365 nm for 15 minutes in an argon gas atmosphere to cause radical polymerization and thereby further grow fluorine-containing functional polymer chains on the polyacrylic acid chains (non-functional polymer chains). In this manner, a surface-modified elastic body (a polymer brush layer on the surface) was obtained.

Example 5

A chlorobutyl rubber (degree of unsaturation: 1 to 2%) containing isoprene units was cross-linked by triazine to prepare a vulcanized rubber gasket (vulcanized at 180° C. for 10 minutes), which was then immersed in a solution of benzophenone in acetone (1 wt %) so that benzophenone was adsorbed onto the surface of the rubber vulcanizate, followed by drying.

The dried vulcanized rubber gasket was immersed in an aqueous acrylamide solution (2.5 M, 17.8 g of acrylamide dissolved in 100 mL of water) in a glass reaction container. Then the gasket was irradiated with LED-UV light having a wavelength of 365 nm for 60 minutes to cause radical polymerization and thereby grow non-functional polymer chains on the surface of the rubber. Then, the surface was washed with water and dried.

Next, the dried vulcanized rubber gasket was immersed in a solution of benzophenone in acetone (1 wt %) so that benzophenone was adsorbed onto the surface of the polyacrylamide, followed by drying. Then a fluorine-containing functional monomer solution (KY-1203 produced by Shin-Etsu Chemical Co., Ltd.) was applied to the surface of the vulcanized rubber gasket where benzophenone was adsorbed on the polyacrylamide surface. Thereafter, the surface was irradiated with LED-UV light having a wavelength of 365 nm for 15 minutes in an argon gas atmosphere to cause radical polymerization and thereby further grow fluorine-containing functional polymer chains on the polyacrylamide chains (non-functional polymer chains). In this manner, a surface-modified elastic body (a polymer brush layer on the surface) was obtained.

Example 6

A chlorobutyl rubber (degree of unsaturation: 1 to 2%) containing isoprene units was cross-linked by triazine to prepare a vulcanized rubber gasket (vulcanized at 180° C. for 10 minutes), which was then immersed in a solution of benzophenone in acetone (1 wt %) so that benzophenone was adsorbed onto the surface of the rubber vulcanizate, followed by drying.

The dried vulcanized rubber gasket was immersed in a mixed aqueous solution containing acrylic acid and acrylamide at a ratio of 25:75 (2.5 M, 4.5 g of acrylic acid and 13.4 g of acrylamide dissolved in 100 mL of water) in a glass reaction container. Then the gasket was irradiated with LED-UV light having a wavelength of 365 nm for 52.5 minutes to cause radical polymerization and thereby grow non-functional polymer chains on the surface of the rubber. Then, the surface was washed with water and dried.

Next, the dried vulcanized rubber gasket was immersed in a solution of benzophenone in acetone (1 wt %) so that benzophenone was adsorbed onto the surfaces of the polyacrylic acid and polyacrylamide, followed by drying. Then a fluorine-containing functional monomer solution (KY-1203 produced by Shin-Etsu Chemical Co., Ltd.) was applied to the surface of the vulcanized rubber gasket where benzophenone was adsorbed on the polyacrylic acid surface and the polyacrylamide surface. Thereafter, the surface was irradiated with LED-UV light having a wavelength of 365 nm for 15 minutes in an argon gas atmosphere to cause radical polymerization and thereby further grow fluorine-containing functional polymer chains on the polyacrylic acid chains and polyacrylamide chains (non-functional polymer chains). In this manner, a surface-modified elastic body (a polymer brush layer on the surface) was obtained.

Example 7

A chlorobutyl rubber (degree of unsaturation: 1 to 2%) containing isoprene units was cross-linked by triazine to prepare a vulcanized rubber gasket (vulcanized at 180° C. for 10 minutes), which was then immersed in a benzophenone-containing aqueous acrylamide solution (2.5 M, a solution prepared by dissolving 17.8 g of acrylamide in 100 mL of water and further dissolving 2 mg of benzophenone therein) in a glass reaction container. Then the gasket was irradiated with LED-UV light having a wavelength of 365 nm for 60 minutes to cause radical polymerization and thereby grow non-functional polymer chains on the surface of the rubber. Then, the surface was washed with water and dried.

Next, a fluorine-containing functional monomer solution (KY-1203 produced by Shin-Etsu Chemical Co., Ltd.) containing dissolved benzophenone in an amount of 3 wt % with respect to the amount of the monomer was applied to the surface of the vulcanized rubber gasket where polyacrylamide was grown. Thereafter, the surface was irradiated with LED-UV light having a wavelength of 365 nm for 15 minutes in an argon gas atmosphere to cause radical polymerization and thereby further grow fluorine-containing functional polymer chains on the polyacrylamide chains (non-functional polymer chains). In this manner, a surface-modified elastic body (a polymer brush layer on the surface) was obtained.

Example 8

A chlorobutyl rubber (degree of unsaturation: 1 to 2%) containing isoprene units was cross-linked by triazine to prepare a vulcanized rubber gasket (vulcanized at 180° C. for 10 minutes), which was then immersed in a solution of 2,4-diethylthioxane in acetone (1 wt %) so that 2,4-diethylthioxane was adsorbed onto the surface of the rubber vulcanizate, followed by drying.

The dried vulcanized rubber gasket was immersed in an aqueous acrylamide solution (2.5 M, 17.8 g of acrylamide dissolved in 100 mL of water) in a glass reaction container. Then the gasket was irradiated with LED-UV light having a wavelength of 365 nm for 20 minutes to cause radical polymerization and thereby grow non-functional polymer chains on the surface of the rubber. Then, the surface was washed with water and dried.

Next, the dried vulcanized rubber gasket was immersed in a solution of 2,4-diethylthioxane in acetone (1 wt %) so that 2,4-diethylthioxane was adsorbed onto the surface of the polyacrylamide, followed by drying. Then a fluorine-containing functional monomer solution (KY-1203 produced by Shin-Etsu Chemical Co., Ltd.) was applied to the surface of the vulcanized rubber gasket where 2,4-diethylthioxane was adsorbed on the polyacrylamide surface. Thereafter, the surface was irradiated with LED-UV light having a wavelength of 365 nm for 10 minutes in an argon gas atmosphere to cause radical polymerization and thereby further grow fluorine-containing functional polymer chains on the polyacrylamide chains (non-functional polymer chains). In this manner, a surface-modified elastic body (a polymer brush layer on the surface) was obtained.

Comparative Example 1

A chlorobutyl rubber (degree of unsaturation: 1 to 2%) containing isoprene units was cross-linked by triazine to prepare a vulcanized rubber gasket (vulcanized at 180° C. for 10 minutes), which was then used as it was.

Comparative Example 2

A surface-modified elastic body was obtained as in Example 1, except that only the fluorine-containing functional polymer chains were grown without forming non-functional polymer chains on the surface of the vulcanized rubber gasket.

The surface-modified elastic bodies prepared in the examples and comparative examples were evaluated by the following methods. Table 1 shows the results.
(Length of Polymer Chain)

To determine the length of the polymer chain formed on the surface of the rubber vulcanizate, a cross section of the modified rubber on which the polymer chains were formed was measured with an SEM at an accelerating voltage of 15 kV and a magnification of 1000 times. The thickness of the polymer layer photographed was determined as the length of the polymer chain.
(Friction Resistance)

To determine the friction resistance of the surface of the surface-modified elastic body, the vulcanized rubber gasket prepared in each of the examples and comparative examples was inserted into a COP resin barrel of a syringe and further pushed (push rate: 30 ram/min) in the barrel using a tensile tester while friction resistance was measured. The values of the examples are expressed as a friction resistance index using the equation below, with the friction resistance of Comparative Example 1 being set equal to 100. A lower index indicates a lower friction resistance.

(Friction resistance index)=(Friction resistance of each example)/(Friction resistance of Comparative Example 1)×100

The results of Table 1 show that the surfaces of the surface-modified elastic bodies obtained in the examples exhibited greatly reduced friction resistances and therefore had good sliding properties. In addition, since only the surface was modified, the sealing properties of these surface-modified elastic bodies were similar to Comparative Example 1.

Thus, when the elastic bodies are used as a gasket of a syringe plunger, they provide sufficient sealing properties while reducing the friction of the plunger with the syringe barrel, and therefore they enable easy and accurate treatment with the syringe. In addition, since they have a small difference between static and kinetic friction coefficients, start of pushing the plunger and the subsequent inward movement of the plunger can be smoothly carried out without pulsation. Moreover, if polymer chains are formed on the inner surface of a syringe barrel formed from a thermoplastic elastomer, treatment with the syringe can be easily accomplished, similarly as above.

Furthermore, the above-mentioned effects can be expected when polymer chains are formed on the surfaces of the grooves on the tread or of the sidewall of tires for use on vehicles such as passenger cars, on the surfaces of diaphragms, on the sliding surfaces of skis or snowboards, or on the surfaces of swimsuits, road signs, sign boards, or the like.

REFERENCE SIGNS LIST

1: Gasket
11a, 11b, 11c: Circular protruding portion
13: Bottom surface
2: Tread portion
3a: Longitudinal center groove
3b: Longitudinal shoulder groove
5: Fine groove
6: Beveled intermediate groove
7: Connecting groove
8, 8a, 8b: lateral shoulder groove

The invention claimed is:
1. A method for surface-modifying an object of a rubber vulcanizate or a thermoplastic elastomer, the method comprising:
step 1 of forming polymerization initiation points A on a surface of the object; and
step 2 of radically polymerizing a non-functional monomer, starting from the polymerization initiation points A, to grow non-functional polymer chains, and further radically polymerizing a fluorine-containing functional monomer to grow fluorine-containing functional polymer chains on the non-functional polymer chains,

TABLE 1

|  | Example | | | | | | | | Comparative Example | |
| --- | --- | --- | --- | --- | --- | --- | --- | --- | --- | --- |
|  | 1 | 2 | 3 | 4 | 5 | 6 | 7 | 8 | 1 | 2 |
| Length of entire polymer chain (nm) | 12000 | 12500 | 13000 | 10500 | 8000 | 9000 | 10000 | 12500 | — | 2000 |
| [Non-functional polymer chain]: [Fluorine-containing functional polymer chain] (in length) | 98:2 | 97:3 | 85:15 | 90:10 | 84:16 | 90:10 | 86:14 | 87:13 | — | — |
| Friction resistance index | 1.25 | 0.825 | 0.82 | 1.30 | 0.92 | 0.80 | 0.96 | 0.87 | 100 | 55 | wherein
the non-functional monomer is at least one selected from the group consisting of acrylic acid, acrylic acid esters, acrylic acid alkali metal salts, acrylic acid amine salts, acrylamide, dimethylacrylamide, diethylacrylamide, isopropylacrylamide, hydroxyethylacrylamide, acryloylmorpholine, methoxymethyl acrylate, hydroxyethyl acrylate, methacrylic acid, methacrylic acid esters, methacrylic acid alkali metal salts, methacrylic acid amine salts, methacrylamide, dimethylmethacrylamide, diethylmethacrylamide, isopropylmethacrylamide, hydroxyethylmethacrylamide, methacryloylmorpholine, methoxymethyl methacrylate, hydroxyethyl methacrylate, and acrylonitrile; and
the fluorine-containing functional monomer is a fluorine-containing (meth)acrylic-modified organic silicon compound that is obtained by an addition reaction of an unsaturated monocarboxylic acid (B) containing a (meth)acrylic group with a fluorine-containing epoxy-modified organic silicon compound (A) represented by the following formula (1):

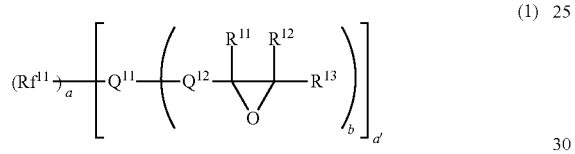

wherein
$Rf^{11}$ represents a monovalent or divalent group having a molecular weight of 100 to 40,000 and containing a fluoroalkyl structure or a fluoropolyether structure;
$Q^{11}$ represents a linking group which comprises a siloxane structure, an unsubstituted or halogen-substituted silalkylene structure, a silarylene structure, or a combination of two or more thereof, each of which contains at least (a+b) silicon atoms and has a valency of (a+b), and $Q^{11}$ may have a cyclic structure;
$Q^{12}$ represents a C1-20 divalent hydrocarbon group and $Q^{12}$ may have a cyclic structure and may be interrupted by an ether linkage or an ester linkage;
$R^{11}$ to $R^{13}$ each independently represent a hydrogen atom or a C1-10 monovalent hydrocarbon group, provided that a part or all of the hydrogen atoms of $R^{11}$ to $R^{13}$ may be replaced with a halogen atom, and $R^{11}$ and $R^{12}$ may be joined to each other to form a ring together with the carbon atoms to which they are attached;
when $Rf^{11}$ is a monovalent group, a' and a represent 1 and an integer of 1 to 6, respectively, and when $Rf^{11}$ is a divalent group, a and a' represent 1 and 2, respectively; and b represents an integer of 1 to 20.

2. The method according to claim 1, wherein the step 1 comprises adsorbing a photopolymerization initiator onto the surface of the object, optionally followed by irradiation with LED light having a wavelength of 300 to 400 nm, to form polymerization initiation points from the photopolymerization initiator on the surface.

3. The method according to claim 1, wherein the step 2 comprises radically polymerizing a non-functional monomer, starting from the polymerization initiation points A, by irradiation with LED light having a wavelength of 300 to 450 nm to grow non-functional polymer chains, and further radically polymerizing a fluorine-containing functional monomer by irradiation with LED light having a wavelength of 300 to 450 nm to grow fluorine-containing functional polymer chains.

4. The method according to claim 1, wherein the rubber vulcanizate or thermoplastic elastomer contains an allylic carbon atom which is a carbon atom adjacent to a double bond.

5. The method according to claim 2, wherein the photopolymerization initiator is at least one of a benzophenone compound and a thioxanthone compound.

6. The method according to claim 3, wherein the method comprises inserting an inert gas into a reaction container and a reaction solution during or before the light irradiation, and polymerizing the monomer in an atmosphere replaced with the inert gas.

7. The method according to claim 1, wherein, in the formula (1), $Rf^{11}$ contains 1 to 500 repeating units of the following formula:

$$-C_iF_{2i}O-$$

wherein i in each unit independently represents an integer of 1 to 6.

8. The method according to claim 1,
wherein, in the formula (1), $Q^{11}$ is represented by the following formula (2):

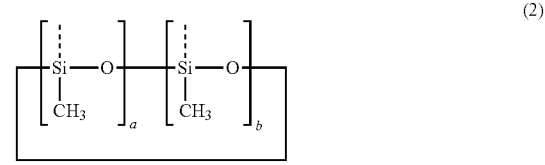

wherein a and b are as defined in the formula (1); the broken lines represent bonds; the unit comprising a repeating unit repeated a times is joined to $Rf^{11}$; the unit comprising a repeating unit repeated b times is joined to a group represented by the following formula:

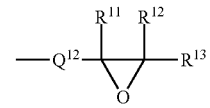

wherein $Q^{12}$ and $R^{11}$ to $R^{13}$ are as defined in the formula (1); the two types of repeating units are randomly arranged; and $Rf^{11}$ is as defined in the formula (1).

9. The method according to claim 1,
wherein, in the formula (1), $Rf^{11}$ is represented by the following formula (3):

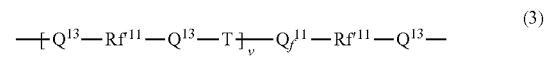

wherein $Rf^{11}$ represents a divalent perfluoropolyether group having a molecular weight of 300 to 30,000 which may be internally branched; $Q^{13}$ represents a divalent organic group which may contain an oxygen atom, a nitrogen atom, a fluorine atom or a silicon atom and may have a cyclic structure or an unsaturated bond; $Q_f^{11}$ represents $Q^{13}$ or a fluorine atom; T represents a linking group represented by the following formula (4):

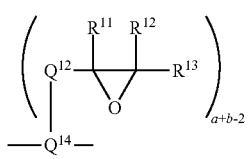

(4)

wherein $R^{11}$ to $R^{13}$, $Q^{12}$, a, and b are as defined in the formula (1), and $Q^{14}$ represents a linking group which comprises a siloxane structure, an unsubstituted or halogen-substituted silalkylene structure, a silarylene structure, or a combination of two or more thereof, each of which contains at least (a+b) silicon atoms and has a valency of (a+b); and v represents an integer of 0 to 5, provided that v is 0 when $Q_f^{11}$ is a fluorine atom.

10. The method according to claim 1, wherein the fluorine-containing functional monomer is a mixture of a fluorine-containing epoxy-modified organic silicon compound represented by the formula below and a fluorine-containing (meth)acrylic-modified organic silicon compound represented by the formula below:

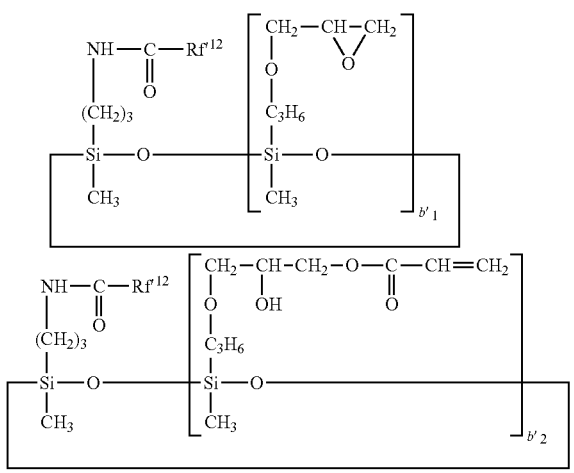

wherein $b'_1+b'_2$ is 2 to 6.5, and $Rf^{12}$ is a group represented by the following formula:

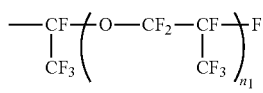

wherein $n_1$ is 2 to 100.

11. The method according to claim 1, wherein the fluorine-containing functional monomer has an infrared absorption spectrum comprising strong absorption peaks at about 1045 cm$^{-1}$ and about 1180 cm$^{-1}$, absorption peaks at about 806 cm$^{-1}$ and about 1720 cm$^{-1}$, a weak absorption peak at about 1532 cm$^{-1}$, and a broad weak absorption peak at about 3350 cm$^{-1}$.

12. The method according to claim 1, wherein the fluorine-containing functional monomer has a $^{13}$C NMR spectrum in chloroform-d solution comprising signals at chemical shifts of about 13.01, 14.63, 23.04, 40.13, 50.65, 63.54, 68.97, 73.76, 76.74, 77.06, 77.38, 113.21, 114.11, 116.96, 117.72, 118.47, 128.06, 131.38, 156.46, and 166.02 ppm.

13. The method according to claim 1, wherein the fluorine-containing functional monomer has a $^1$H NMR spectrum in chloroform-d solution comprising signals at chemical shifts of about 3.40, 3.41, 3.49, 3.60, 5.26, 5.58, 6.12, 6.14, 6.40, 6.42, and 6.46 ppm.

14. The method according to claim 1, wherein the non-functional monomer, the fluorine-containing functional monomer, or a solution thereof contains a polymerization inhibitor, and is polymerized in the presence of the polymerization inhibitor.

15. The method according to claim 14, wherein the polymerization inhibitor is 4-methylphenol.

16. The method according to claim 1, wherein a length of the entire polymer chain, including the non-functional polymer chain and the fluorine-containing functional polymer chain, is 10 to 50000 nm.

17. The method according to claim 1, wherein a ratio between a length of the non-functional polymer chain and a length of the fluorine-containing functional polymer chain is 50:50 to 99.9:0.1.

18. A surface-modified elastic body, which is obtained by a method for surface-modifying an object of a rubber vulcanizate or a thermoplastic elastomer, the method comprising:
step 1 of forming polymerization initiation points A on a surface of the object; and
step 2 of radically polymerizing a non-functional monomer, starting from the polymerization initiation points A, to grow non-functional polymer chains, and further radically polymerizing a fluorine-containing functional monomer to grow fluorine-containing functional polymer chains on the non-functional polymer chains,
wherein
the non-functional monomer is at least one selected from the group consisting of acrylic acid, acrylic acid esters, acrylic acid alkali metal salts, acrylic acid amine salts, acrylamide, dimethylacrylamide, diethylacrylamide, isopropylacrylamide, hydroxyethylacrylamide, acryloylmorpholine, methoxymethyl acrylate, hydroxyethyl acrylate, methacrylic acid, methacrylic acid esters, methacrylic acid alkali metal salts, methacrylic acid amine salts, methacrylamide, dimethylmethacrylamide, diethylmethacrylamide, isopropylmethacrylamide, hydroxyethylmethacrylamide, methacryloylmorpholine, methoxymethyl methacrylate, hydroxyethyl methacrylate, and acrylonitrile; and
the fluorine-containing functional monomer is a fluorine-containing (meth)acrylic-modified organic silicon compound that is obtained by an addition reaction of an unsaturated monocarboxylic acid (B) containing a (meth)acrylic group with a fluorine-containing epoxy-modified organic silicon compound (A) represented by the following formula (1):

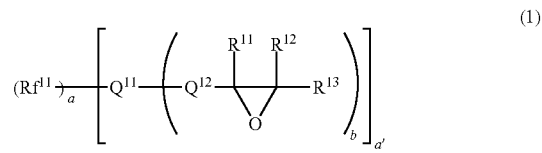

(1)

wherein
$Rf^{11}$ represents a monovalent or divalent group having a molecular weight of 100 to 40,000 and containing a fluoroalkyl structure or a fluoropolyether structure;

$Q^{11}$ represents a linking group which comprises a siloxane structure, an unsubstituted or halogen-substituted silalkylene structure, a silarylene structure, or a combination of two or more thereof, each of which contains at least (a+b) silicon atoms and has a valency of (a+b), and $Q^{11}$ may have a cyclic structure;

$Q^{12}$ represents a C1-20 divalent hydrocarbon group and $Q^{12}$ may have a cyclic structure and may be interrupted by an ether linkage or an ester linkage;

$R^{11}$ to $R^{13}$ each independently represent a hydrogen atom or a C1-10 monovalent hydrocarbon group, provided that a part or all of the hydrogen atoms of $R^{11}$ to $R^{13}$ may be replaced with a halogen atom, and $R^{11}$ and $R^{12}$ may be joined to each other to form a ring together with the carbon atoms to which they are attached;

when $Rf^{11}$ is a monovalent group, a' and a represent 1 and an integer of 1 to 6, respectively, and when $Rf^{11}$ is a divalent group, a and a' represent 1 and 2, respectively; and b represents an integer of 1 to 20.

19. The surface-modified elastic body according to claim 18, comprising a three-dimensional solid that has at least part of its surface modified.

20. The surface-modified elastic body according to claim 18, which comprises a polymer brush.

21. The surface-modified elastic body according to claim 18, which is a gasket for syringes that has at least part of its surface modified.

22. The surface-modified elastic body according to claim 18, which is a tire that has at least part of at least one of a groove surface and a sidewall surface modified.

* * * * *